US011686736B2

United States Patent
Ballantyne et al.

(10) Patent No.: US 11,686,736 B2
(45) Date of Patent: Jun. 27, 2023

(54) BIOMARKERS TO IMPROVE PREDICTION OF HEART FAILURE RISK

(71) Applicants: Christie Mitchell Ballantyne, Houston, TX (US); Ron Hoogeveen, Houston, TX (US); Vijay Nambi, Houston, TX (US); Lloyd E. Chambless, Chapel Hill, NC (US)

(72) Inventors: Christie Mitchell Ballantyne, Houston, TX (US); Ron Hoogeveen, Houston, TX (US); Vijay Nambi, Houston, TX (US); Lloyd E. Chambless, Chapel Hill, NC (US)

(*) Notice: Subject to any disclaimer, the term of this patent is extended or adjusted under 35 U.S.C. 154(b) by 0 days.

(21) Appl. No.: 15/922,431

(22) Filed: Mar. 15, 2018

(65) Prior Publication Data

US 2018/0203022 A1 Jul. 19, 2018

Related U.S. Application Data

(63) Continuation of application No. 14/870,155, filed on Sep. 30, 2015, now abandoned, which is a (Continued)

(51) Int. Cl.
*G01N 33/68* (2006.01)
*G16H 50/30* (2018.01)
*G01N 33/74* (2006.01)

(52) U.S. Cl.
CPC ..... *G01N 33/6893* (2013.01); *G01N 33/6887* (2013.01); *G01N 33/74* (2013.01); (Continued)

(58) Field of Classification Search
CPC ......... G01N 33/6893; G01N 2800/324; G01N 2800/32; G01N 2800/325; G01N 2333/58;
(Continued)

(56) References Cited

U.S. PATENT DOCUMENTS 5,744,305 A 4/1998 Fodor et al.
7,264,939 B2 9/2007 Borgya et al.
(Continued)

FOREIGN PATENT DOCUMENTS

EP 0648228 B1 11/1998
WO 2002/083913 A1 10/2002
(Continued)

OTHER PUBLICATIONS

Sundstrom et al. (European Heart Journal 2009;30,773-781).*
(Continued)

*Primary Examiner* — Gailene Gabel
(74) *Attorney, Agent, or Firm* — Stinson LLP

(57) ABSTRACT

The present disclosure relates to the field of laboratory diagnostics. Specifically, methods are disclosed for determining a patient's risk of suffering from heart failure (HF) based on the detection of NT-proBNP, troponin T, and/or a natriuretic peptide. Also disclosed are methods for improving both the accuracy and speed of HF risk models by incorporating biomarker data from patient samples.

11 Claims, 6 Drawing Sheets

Related U.S. Application Data continuation of application No. 14/068,816, filed on Oct. 31, 2013, now abandoned.

(60) Provisional application No. 61/721,475, filed on Nov. 1, 2012.

(52) U.S. Cl.
CPC ..... *G16H 50/30* (2018.01); *G01N 2333/4712* (2013.01); *G01N 2333/58* (2013.01); *G01N 2800/325* (2013.01); *G01N 2800/50* (2013.01); *G01N 2800/52* (2013.01)

(58) Field of Classification Search
CPC . G01N 2800/50; G01N 33/6887; G01N 33/74
See application file for complete search history.

(56) References Cited

U.S. PATENT DOCUMENTS

| | | | |
|---|---|---|---|
| 7,790,397 | B2 | 9/2010 | Hamm et al. |
| 7,807,380 | B2 | 10/2010 | Borgya et al. |
| 8,361,800 | B2 | 1/2013 | Hess et al. |
| 2008/0076134 | A1 | 3/2008 | Muraca |
| 2011/0107821 | A1 | 5/2011 | Hess et al. |
| 2013/0262357 | A1* | 10/2013 | Amarasingham ...... G16H 50/30 706/21 |
| 2014/0065648 | A1 | 3/2014 | Wienhues-Thelen et al. |

FOREIGN PATENT DOCUMENTS

| | | | |
|---|---|---|---|
| WO | 2002/089657 | A2 | 11/2002 |
| WO | 2008/017928 | A2 | 2/2008 |
| WO | 2010/007041 | A1 | 1/2010 |

OTHER PUBLICATIONS

Agarwal et al. (Circ Heart Fail. 2012;5:422-429; originally published online May 15, 2012).*
Wang et al., (J Am Soc Nephrol 19: 1643-1652, 2008).*
Saunders et al. (Circulation, 2011 vol. 123, pp. 1367-1376).*
Chenevier-Gobeaux (Ann. Clin Biochem 2011;48:452-458.*
Agarwal, Sunil K. et al., Prediction of Incident Heart Failure in General Practice the Atherosclerosis Risk in Communities (ARIC) Study, Circulation Heart Failure, 2012, pp. 422-429, vol. 5, No. 4.
Agarwal, Sunil K. et al., Sources of Variability in Measurements of Cardiac Troponin T in a Community-Based Sample: The Atherosclerosis Risk in Communities Study, Clinical Chemistry, 2011, pp. 891-897, vol. 57, No. 6.
Ammar, Khawaja Afzal et al., Prevalence and Prognostic Significance of Heart Failure Stages, Circulation, 2007, pp. 1563-1570, vol. 115, No. 12.
Anderson, Page A. W. et al., Molecular Basis of Human Cardiac Troponin T Isoforms Expressed in the Developing, Adult, and Failing Heart, Circulation Research, 1995, pp. 681-686, vol. 76.
Bayés-Genís, Antoni et al.. N-terminal probrain natriuretic peptide (NT-proBNP) in the emergency diagnosis and in-hospital monitoring of patients with dyspnoea and ventricular dysfunction, The European Journal of Heart Failure, 2004, pp. 301-308, vol. 6.
Bhalla, Vikas et al., B-Type Natriuretic Peptide: The Level and the Drug—Partners in the Diagnosis and Management of Congestive Heart Failure, Congestive Heart Failure, 2004, pp. 3-27, vol. 10 (1 Supplement 1).
Bonnevie, Lise et al., The use of computerized decision support systems in preventive cardiology-principal results from the national PRECARD® survey in Denmark, European Journal of Cardiovascular Prevention and Rehabilitation, 2005, pp. 52-55, vol. 12, No. 1.
Bonow, Robert O., New Insights Into the Cardiac Natriuretic Peptides, Circulation, 1996, pp. 1946-1950, vol. 93.
Butler, Javed et al., Incident Heart Failure Prediction in the Elderly the Health ABC Heart Failure Score, Circulation Heart Failure, 2008, pp. 125-133, vol. 1.
Chamberlain, Alanna M. et al., A Clinical Risk Score for Atrial Fibrillation in a Biracial Prospective Cohort (from the Atherosclerosis Risk in Communities [ARIC] Study), American Journal of Cardiology, 2011, pp. 85-91, vol. 107.
Cortés-Sanabria, Laura et al., Improving Care of Patients With Diabetes and CKD: A Pilot Study for a Cluster-Randomized Trial, American Journal of Kidney Diseases, 2008, pp. 777-788, vol. 51.
De Antonio, Marta et al., Combined use of high-sensitivity cardiac troponin T and N-terminal pro-B type natriuretic peptide improves measurements of performance over established mortality risk factors in chronic heart failure, American Heart Journal, 2012, pp. 821-828, vol. 163.
Ferrieres, Gaelle et al., Human cardiac troponin I: precise identification of antigenic epitopes and prediction of secondary structure, Clinical Chemistry, 1998, pp. 487-493, vol. 44, No. 3.
Folsom, Aaron R. et al., Absolute and Attributable Risks of Heart Failure Incidence in Relation to Optimal Risk Factors, Circulation Heart Failure, 2009, pp. 11-17, vol. 2.
Folsom, Aaron R et al., Troponin T, NT-pro BNP, and Incidence of Stroke: The Atherosclerosis Risk in Communities (ARIC) Study, Stroke, 2013, pp. 961-967, vol. 44, No. 4.
Grønnesby, Jon Ketil and BORGAN, Ørnulf, A Method for Checking Regression Models in Survival Analysis Based on the Risk Score, Lifetime Data Analysis, 1996, pp. 315-328, vol. 2.
Hanley, James A. and McNeil, Barbara J., The Meaning and Use of the Area under a Receiver Operating Characteristic (ROC) Curve, Radiology, 1982, pp. 29-36, vol. 143.
Harrell, Frank E. Jr., et al., Tutorial in Biostatistics Multivariable Prognostic Models: Issues in Developing Models, Evaluating Assumptions and Adequacy, and Measuring and Reducing Errors, Statistics in Medicine, 1996, pp. 361-387, vol. 15.
Heidenreich, Paul A. et al., Forecasting the Future of Cardiovascular Disease in the United States a Policy Statement From the American Heart Association, Circulation, 2011, pp. 933-944, vol. 123.
Hermsen, D. et al., Results from a Multicenter Evaluation of the 4th Generation Elecsys® Troponin T assay, Clinical Laboratory, 2007, pp. 1-9, vol. 53.
Hobbs, FD Richard and Erhardt, Leif, Acceptance of guideline recommendations and perceived implementation of coronary heart disease prevention among primary care physicians in five European countries: the Reassessing European Attitudes about Cardiovascular Treatment (REACT) survey, Family Practice, 2002, pp. 596-604, vol. 19, No. 3.
Hunt, Sharon A et al., ACC/AHA Guidelines for the Evaluation and Management of Chronic Heart Failure in the Adult: Executive Summary, Circulation, 2001, pp. 2996-3007, vol. 104.
Hunt, Sharon Ann et al., ACC/AHA 2005 Guideline Update for the Diagnosis and Management of Chronic Heart Failure in the Adult, Journal of the American College of Cardiology, 2005, pp. e1-e82, vol. 46.
International Search Report dated Jan. 7, 2014, in Application No. PCT/EP2013/072943, 5 pages.
Ishii, Junnichi et al., Risk Stratification Using a Combination of Cardiac Troponin T and Brain Natriuretic Peptide in Patients Hospitalized for Worsening Chronic Heart Failure, American Journal of Cardiology, 2002, pp. 691-695, vol. 89.
Johnson, David W. et al., Chronic kidney disease and measurement of albuminuria or proteinuria: a position statement, Medical Journal of Australia, 2012, pp. 224-225, vol. 197, No. 4.
Kalogeropoulos, Andreas P. et al., Echocardiography, Natriuretic Peptides, and Risk for Incident Heart Failure in Older Adults, Journal of the American College of Cardiology, 2012, pp. 131-140, vol. 5, No. 2.
Kannel, William B. et al., Profile for Estimating Risk of Heart Failure, Archives of Internal Medicine, 1999, pp. 1197-1204, vol. 159, No. 2.
Mosca, Lori et al., National Study of Physician Awareness and Adherence to Cardiovascular Disease Prevention Guidelines, Circulation, 2005, pp. 499-510, vol. 111.
Mueller, Thomas et al., Long-term stability of endogenous B-type natriuretic peptide (BNP) and amino terminal proBNP (NT-

(56) References Cited

OTHER PUBLICATIONS proBNP) in frozen plasma samples, Clinical Chemistry & Laboratory Medicine, 2004, pp. 942-944, vol. 12, No. 8.

Nambi, Vijay et al., Carotid Intima-Media Thickness and Presence or Absence of Plaque Improves Prediction of Coronary Heart Disease Risk, Journal of the American College of Cardiology, 2010, pp. 1600-1607, vol. 55, No. 15.

Nambi, Vijay et al., Troponin T and N-Terminal Pro-B-Type Natriuretic Peptide: A Biomarker Approach to Predict Heart Failure Risk—The Atherosclerosis Risk in Communities Study, Clinical Chemistry, 2013, pp. 1802-1810, vol. 59, No. 12.

Needleman, Saul B. and Wunsch, Christian D., A General Method Applicable to the Search for Similarities in the Amino Acid Sequence of Two Proteins, Journal of Molecular Biology, 1970, pp. 443-453, vol. 48.

Nolan, John P. and Sklar, Larry A., Suspension array technology: evolution of the flat-array paradigm, Trends in Biotechnology, 2002, pp. 9-12, vol. 20, No. 1.

Pearson, William R. and Lipman, David J., Improved tools for biological sequence comparison, Proceedings of the National Academy of Sciences USA, 1988, pp. 2444-2448, vol. 85.

Pencina, Michael J. et al., Extensions of net reclassification improvement calculations to measure usefulness of new biomarkers, Statistics in Medicine, 2011, pp. 11-21, vol. 30.

Polonsky, Tamar S. et al., Coronary Artery Calcium Score and Risk Classification for Coronary Heart Disease Prediction, JAMA, 2010, pp. 1610-1616, vol. 303, No. 16.

Saunders, Justin T. et al., Cardiac Troponin T Measured by a Highly Sensitive Assay Predicts Coronary Heart Disease, Heart Failure, and Mortality in the Atherosclerosis Risk in Communities Study, Circulation, 2011, pp. 1367-1376, vol. 123.

Smith, M. W. et al., Delayed metabolism of human brain natriuretic peptide reflects resistance to neutral endopeptidase. Journal of Endocrinology, 2000, pp. 239-246, vol. 167.

Smith, Temple F. and Waterman, Michael S., Comparison of Biosequences, Advances in Applied Mathematics, 1981, pp. 482-489, vol. 2.

Sundström, Johan et al., Cardiac troponin-I and risk of heart failure: a community-based cohort study, European Heart Journal, 2009, pp. 773-781, vol. 30.

Taniguchi, Ryoji et al., Combined Measurements of Cardiac Troponin T and N-Terminal Pro-Brain Natriuretic Peptide in Patients With Heart Failure, Circulation Journal, 2004, pp. 1160-1164, vol. 68.

Wang, Angela Yee-Moon and Lai, Kar-Neng, Use of Cardiac Biomarkers in End-Stage Renal Disease, Journal of the American Society of Nephrology, 2008, pp. 1643-1652, vol. 19.

Wu, Alan H. B. et al., Analytical and Clinical Evaluation of the Bayer ADVIA Centaur Automated B-Type Natriuretic Peptide Assay in Patients with Heart Failure: A Multisite Study, Clinical Chemistry, 2004, pp. 867-873, vol. 50, No. 5.

Youden, W. J., Index for Rating Diagnostic Tests, Cancer, 1950, pp. 32-35, vol. 3, Issue 1.

\* cited by examiner

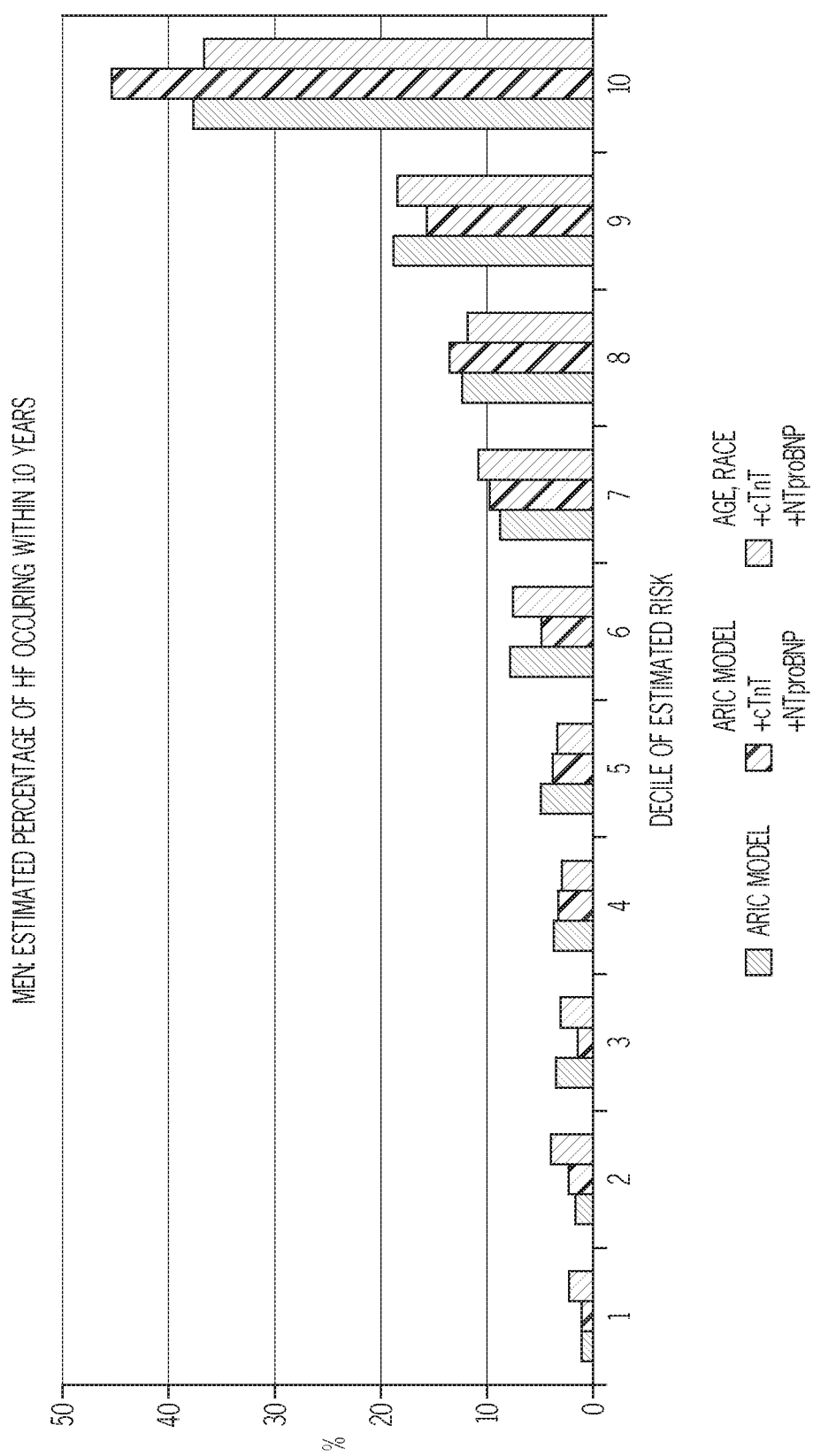
FIG. 1.1

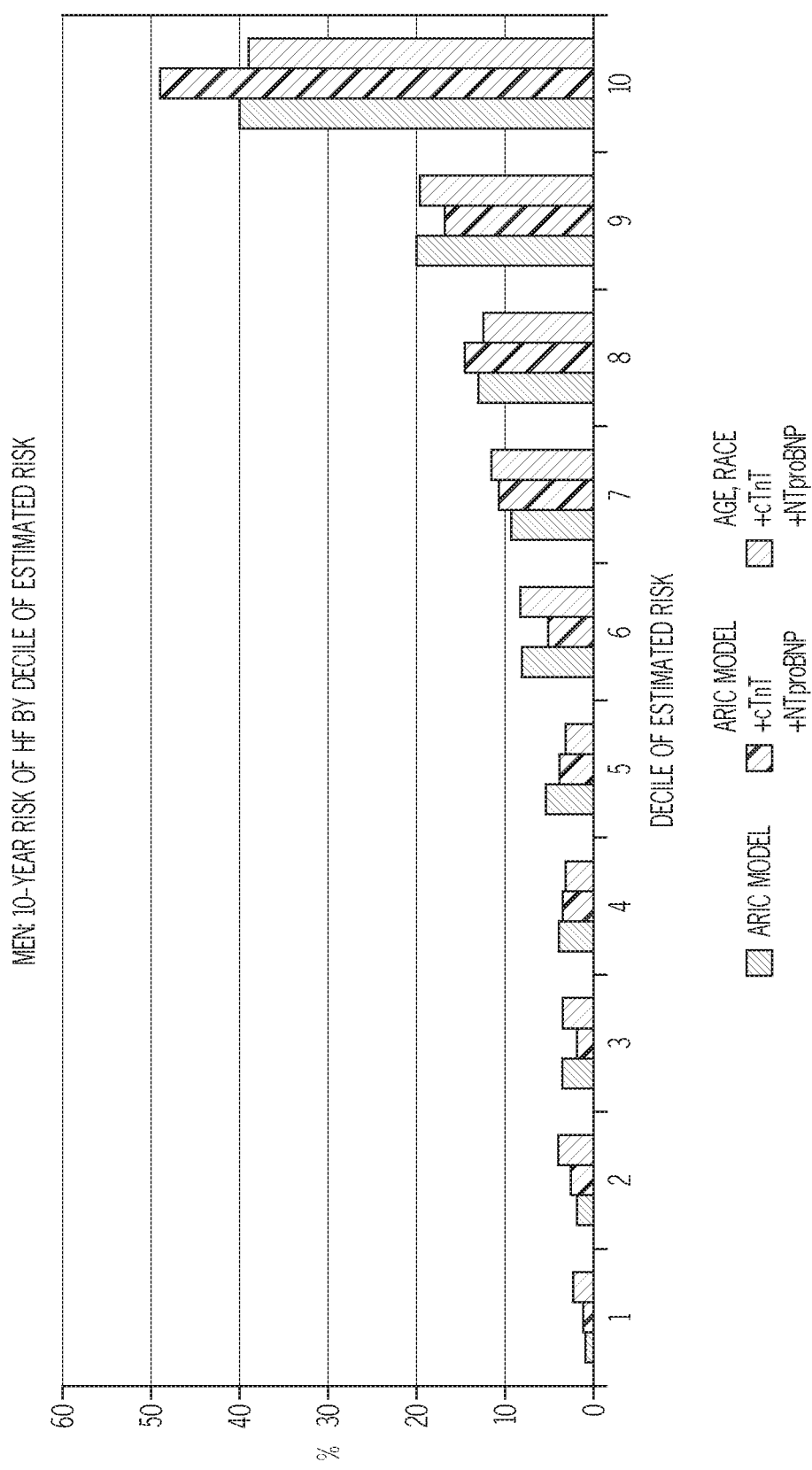
FIG. 1.2

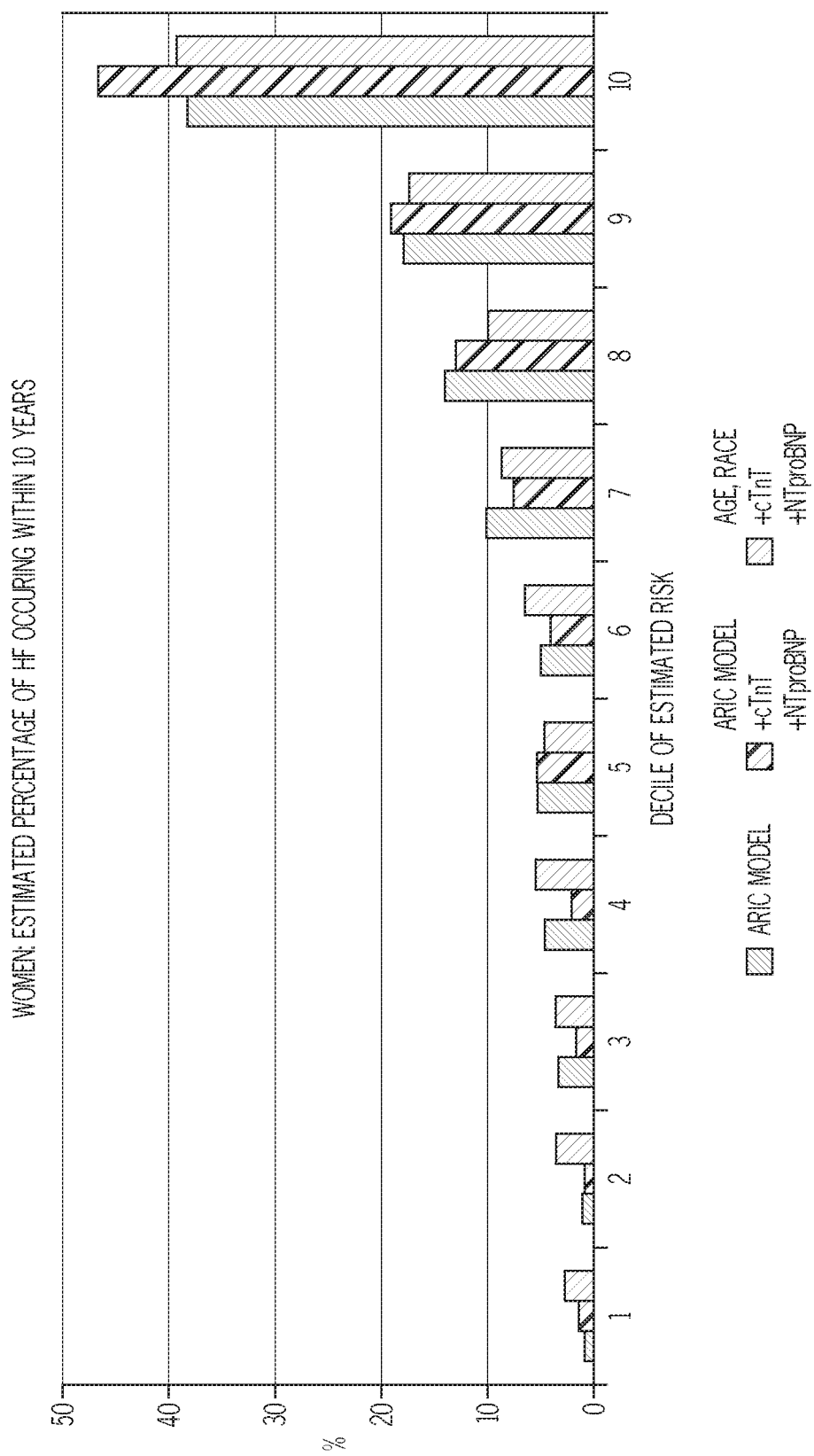
FIG. 2.1

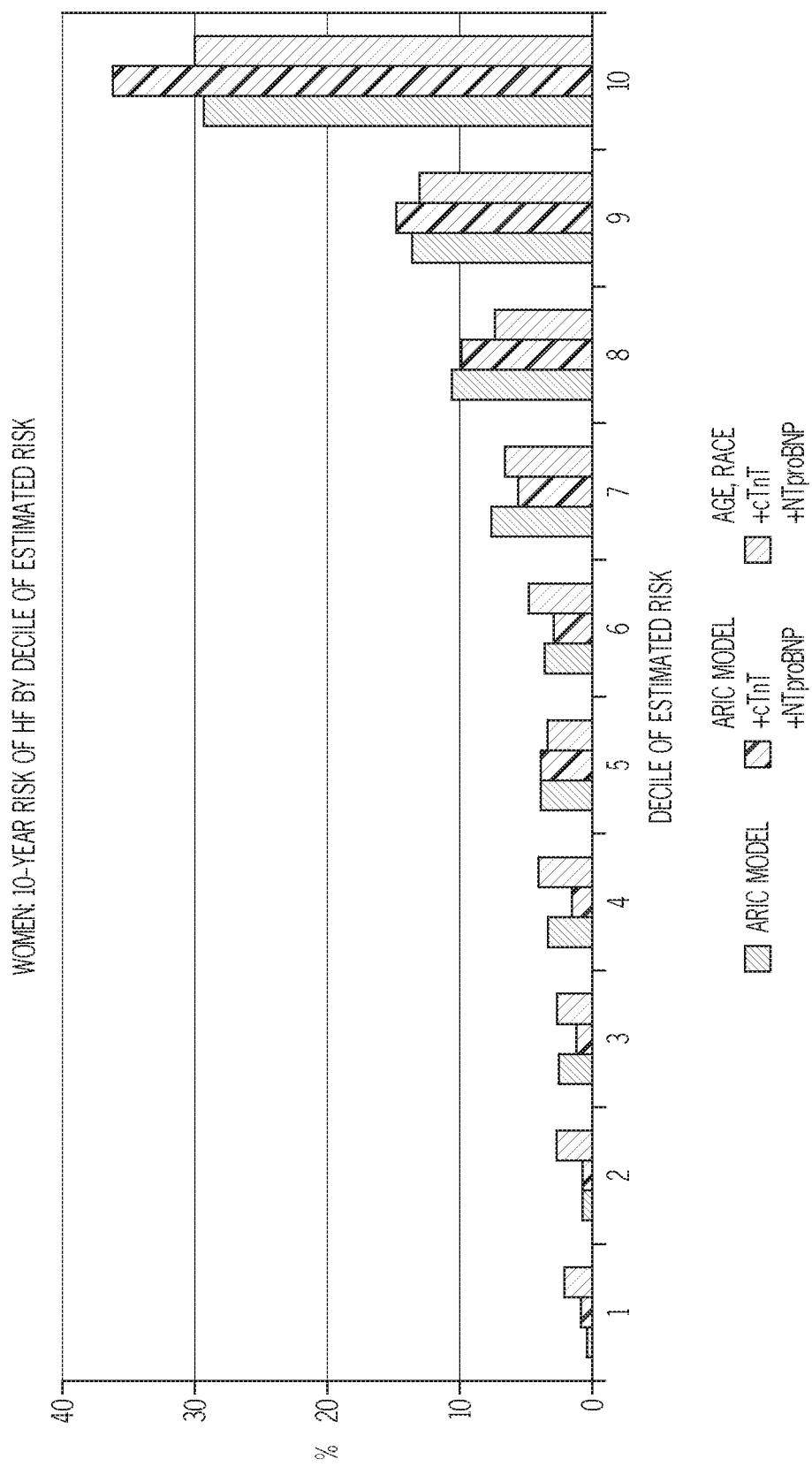
FIG. 2.2

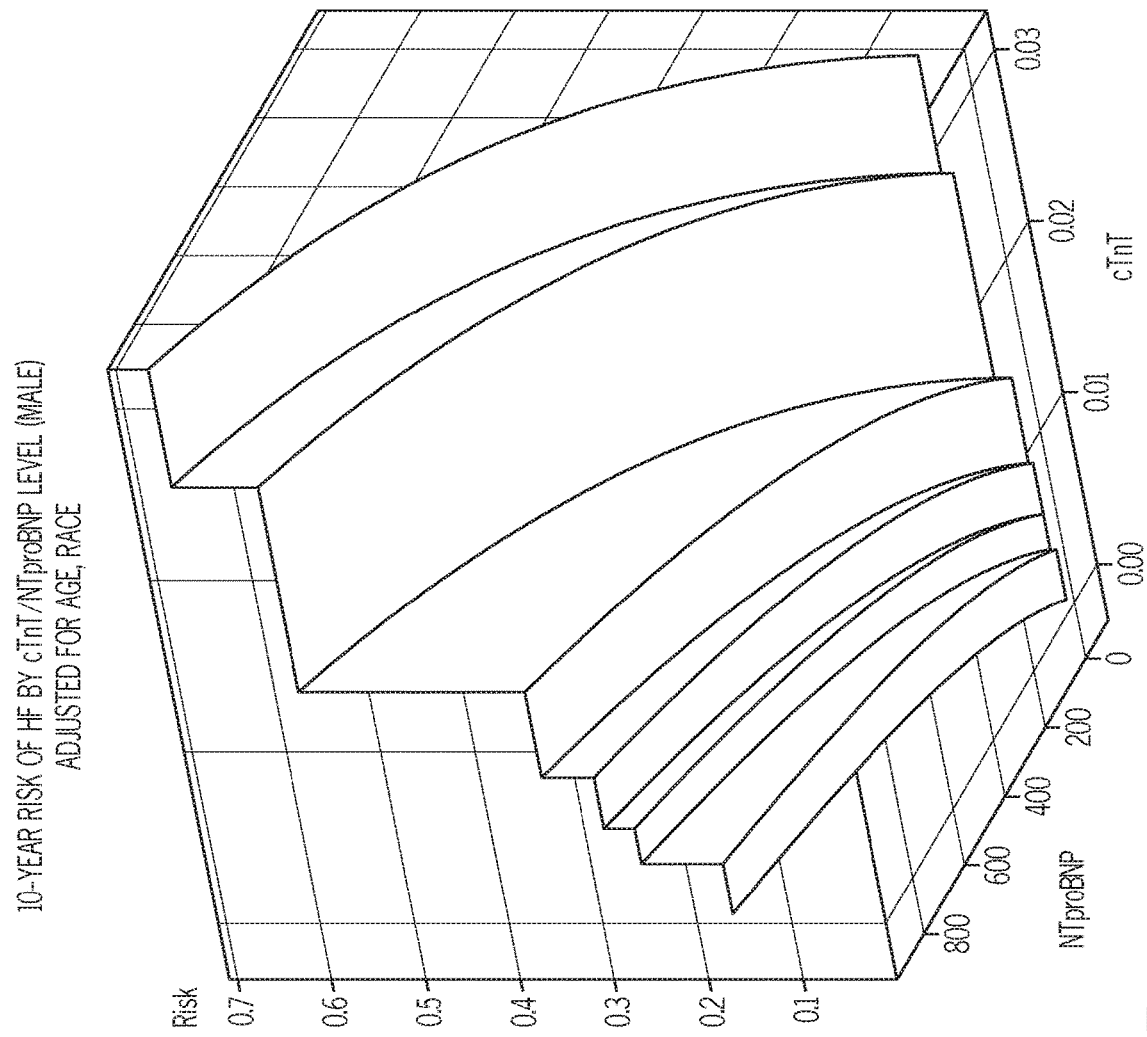
FIG. 3.1

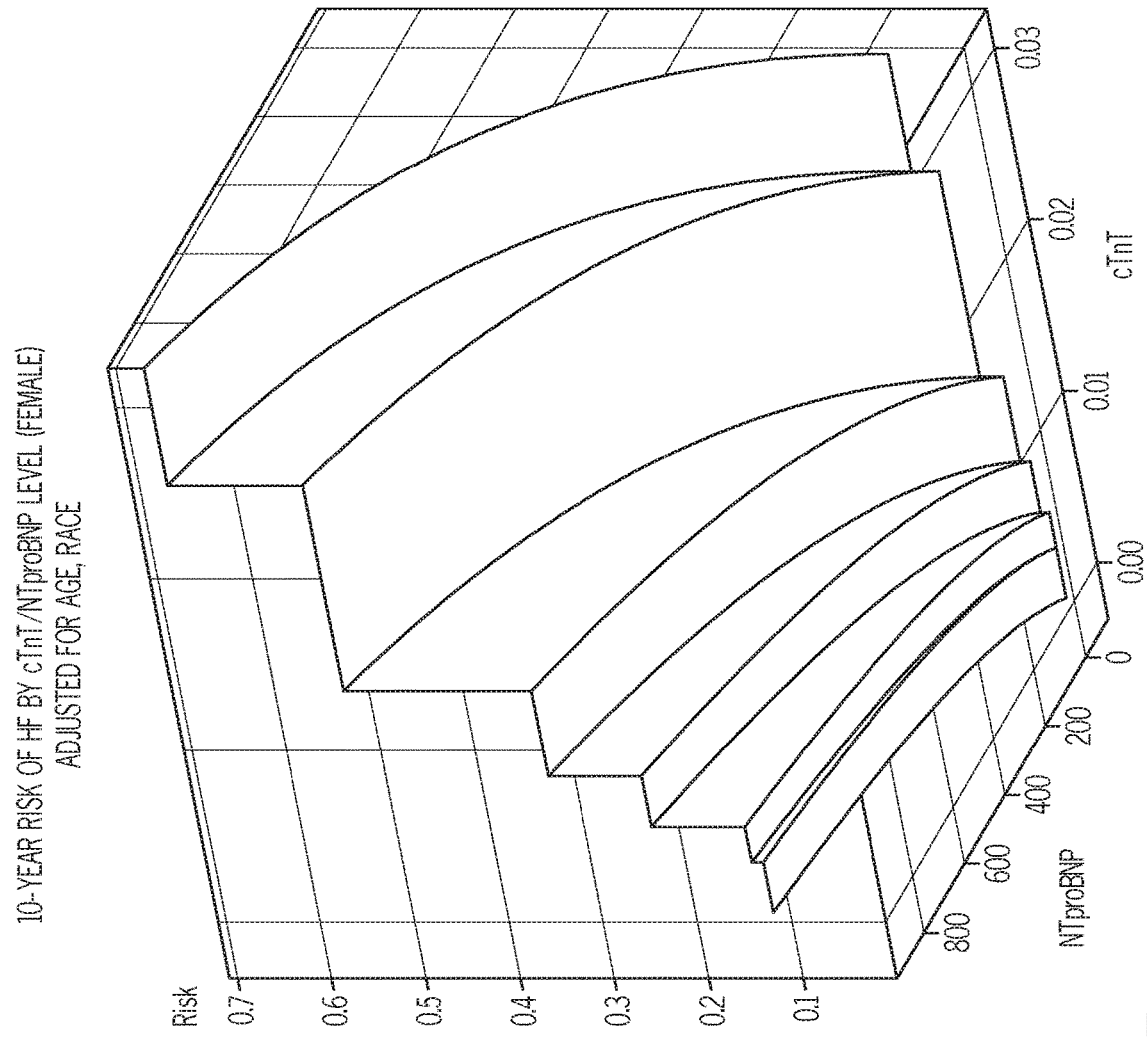
FIG. 3.2

BIOMARKERS TO IMPROVE PREDICTION OF HEART FAILURE RISK

CROSS REFERENCE TO RELATED APPLICATIONS

This application is a continuation of U.S. application Ser. No. 14/870,155 filed Sep. 30, 2015 (abandoned), which is a continuation of Ser. No. 14/068,816 filed Oct. 31, 2013 (abandoned), which claims the benefit of U.S. Provisional Application No. 61/721,475 filed Nov. 1, 2012, the disclosures of which are hereby incorporated by reference in their entirety.

The invention described herein was made with U.S. government support under contracts HHSN268201100005C, HHSN268201100006C, HHSN268201100007C, HHSN268201100008C, HHSN268201100009C, HHSN2682011000100, HHSN268201100011C, and HHSN268201100012C awarded by the National Heart, Lung, and Blood Institute. The U.S. government has certain rights in the invention.

TECHNICAL FIELD

The present disclosure relates to the field of laboratory diagnostics.

BACKGROUND OF THE DISCLOSURE

Among the various cardiovascular diseases, heart failure is projected to have the largest increases in incidence over the coming decades (Heidenreich, *Circulation.* 2011, 123 (8): 933-44). As a matter of public health, it is of critical importance to identify patients at risk for heart failure. Preventative changes in diet, behavior, lifestyle, and other factors can dramatically decrease a patient's likelihood of experiencing heart failure, particularly if the risk is identified early. However, diagnosing patients at risk for heart failure remains difficult, particularly due to the limitations of the currently available methods of heart failure prediction.

Consequently, the technical problem underlying the present disclosure could be seen as the provision of improved means and methods for identifying individuals that have an elevated risk of heart failure. The problem is solved by the embodiments of the present disclosure and described in the claims and in the specification below.

SUMMARY OF THE DISCLOSURE

The present disclosure relates to the field of laboratory diagnostics. In one aspect, methods for an improved diagnosis of heart failure (HF) risk in a patient are disclosed. Specifically, the diagnosis of risk of HF in a patient can be improved by determining the amount of specific biomarkers in the patient's sample, and combining this data with patient data. In one aspect, some or all of the patient data from clinical HF risk models can be used to improve the diagnosis of HF risk, including for example improving the accuracy of the diagnosis. In another aspect, combining the biomarker amounts with only a small subset of readily obtainable patient data can be used to improve the diagnosis of HF risk, including for example improving the speed of the diagnosis. In one aspect, the biomarkers measured are troponin and/or natriuretic peptide.

The methods of the present disclosure may be carried out manually or may be automated. One or more steps of the disclosed methods may be automated, e.g., by suitable robotic and sensory equipment for determining the amount of troponin and/or natriuretic peptide in a patient sample, or by a computer-implemented step of comparing the amount of troponin and/or natriuretic peptide determined in a sample from a patient with a suitable reference amount.

The above-described embodiments of the various aspects of the disclosure may be used alone or in any combination thereof without departing from the scope of the disclosure. Specific aspects will become evident from the following more detailed description and the claims.

BRIEF DESCRIPTION OF THE DRAWINGS

A better understanding of the disclosure may be obtained in light of the following drawings which are set forth for illustrative purposes, and should not be construed as limiting the scope of the disclosure in any way.

FIG. 1.1: Distribution (%) of HF Events Within 10 years Over Deciles of Estimated Risk for Men. Distribution of heart failure (HF) events in men within 10 years over decile of estimated risk according to the ARIC model, the ARIC+ cTnT and NT-proBNP model, and the age, race+cTnT and NT-proBNP model. Note: Troponin modeled as 6-categories and NT-proBNP log transformed. The ARIC heart failure risk prediction model, or ARIC Model, comprises several components, such as age, race, gender, systolic blood pressure, diastolic blood pressure, anti-hypertensive medication use, current/former smoking, diabetes, body mass index (BMI), prevalent coronary heart disease and heart rate.

FIG. 1.2: Ten Year Risk of HF by Decile of Estimated Risk for Men. Ten year risk of heart failure (HF) events in men by decile of estimated risk according to the ARIC model, the ARIC+cTnT and NT-proBNP model, and the age, race+cTnT and NT-proBNP model. Troponin modeled as 6-categories. NT-proBNP is log transformed. ARIC Model is as described previously herein.

FIG. 2.1: Distribution (%) of HF Events Within 10 Years Over Deciles of Estimated Risk for Women. Distribution of heart failure (HF) events in women within 10 years over decile of estimated risk according to the ARIC model, the ARIC+cTnT and NT-proBNP model, and the age, race+ cTnT and NT-proBNP model. Troponin modeled as 6-categories. NT-proBNP is log transformed. ARIC Model is as described previously herein.

FIG. 2.2: Ten Year Risk of HF by Decile of Estimated Risk for Women. Ten year risk of heart failure (HF) events in women by decile of estimated risk according to the ARIC model, the ARIC+cTnT and NT-proBNP model, and the age, race+cTnT and NT-proBNP model.

FIG. 3.1: 10-Year Risk of HF by cTnT/NT-proBNP Levels in Men. Ten year risk of heart failure (HF) events by cTnT/NT-proBNP in men, adjusted for age and race.

FIG. 3.2: 10-Year Risk of HF by cTnT/NT-proBNP Levels in Women. Ten year risk of heart failure (HF) events by cTnT/NT-proBNP in women, adjusted for age and race.

DETAILED DESCRIPTION OF THE EMBODIMENTS

The embodiments disclosed herein are not intended to be exhaustive or limit the disclosure to the precise form disclosed in the following detailed description. Rather, the embodiments are chosen and described so that others skilled in the art may utilize their teachings.

The term "heart failure" or "HF" has previously been described in the Atherosclerosis Risk in Communities (ARIC) study (Agarwal, et al., *Circ Heart Fail.* 2012; 5(4):

422-9). Briefly, hospital discharge records that used an ICD-9 code of 428.x in any position, or death certificates that used ICD-9 or ICD-10 codes of 428.x or 150, respectively, were considered to be an indication of HF. Although a number of effective evidence-based therapies have been developed to treat symptomatic HF, long-term outcomes remain poor. Hence, prevention and prediction of HF remain important goals.

The term "predicting the risk" as used herein refers to assessing the probability that a subject will suffer from HF within a certain time window, i.e., the predictive window. However, as will be understood by those skilled in the art, such an assessment is usually not intended to be binding for each and every subject being investigated. The term, however, requires that a prediction can be made for a statistically significant portion of subjects in a proper and correct manner. Whether a portion is statistically significant can be determined by those skilled in the art using various well known statistic evaluation tools, e.g., determination of confidence intervals, p-value determination, Student's t-test, and Mann-Whitney test. Details regarding suitable statistic evaluation tools can be found in Dowdy and Wearden, *Statistics for Research* (John Wiley & Sons, New York 1983). Suitable confidence intervals are at least 90%, at least 95%, at least 97%, at least 98%, or at least 99%. Suitable p-values are 0.1, 0.05, 0.01, 0.005, or 0.0001.

One current approach to HF risk prediction was created to facilitate prevention and early diagnosis of individuals at risk. The American College of Cardiology/American Heart Association (AHA) HF writing committee proposed a simple new A through D staging system for HF, where for example stages A and B were defined as those having the risk factors or milieu to develop HF, but without clinical symptoms (Hunt et al., 2005, *J. Am. Coll Cardiol.* 46(6): e1-82, Hunt et al., 2001, *Circulation.* 104(24): 2996-3007). Though simpler than other existing risk assessments, the simplicity of the staging system also introduces limitations. For example, in a random population, this staging system identified the majority of individuals 45 years of age or older as Stages A or B (about 56 percent) (Ammar et al., 2007, *Circulation.* 115(12): 1563-70). Therefore, a great majority of asymptomatic individuals are classified as "at risk" and only a minority develop HF. This over-identification indicates that improvements to risk stratification may be needed.

To improve the accuracy of risk prediction, clinical risk prediction tools have emerged over the past decade, such as the Health ABC (Butler et al., 2008, *Circ Heart Fail.* 1(2): 125-33), the Framingham HF risk score (Kannel et al., 1999, *Arch Intern Med.* 159(11): 1197-204), and more recently, the Atherosclerosis Risk in Communities (ARIC) HF score (Agarwal et al., 2012, *Circ Heart Fail.* 5(4): 422-29). However, adoption of clinical risk scores by physicians has been poor, with certain studies reporting that only ~50% physicians use them in practice, suggesting that these clinical risk scores also comprise significant shortcomings (Mosca, et al., 2005, *Circulation.* 111(4): 499-510). Other European studies have reported even less use of clinical risk scores (Bonnevie L, et al., 2005, *European J. Cardio. Prev. Rehab.* 12(1): 52-5; Hobbs et al., 2002, *Family Practice.* 19(6): 596-604).

The ARIC study is a prospective bi-racial (Whites and Blacks) study of cardiovascular disease incidence, in which subjects (n=15,792) were recruited from four communities in the United States between 1987 and 1989. This study provides an example of how clinical risk scores can be generated (Chamberlain A. M. et al., 2011, *Am J Cardiol.* 107(1): 85-91). Participants received an extensive examination, including medical, social, and demographic data. Study participants were reexamined every three years with the first examination (baseline) occurring in 1987-89, the second in 1990-92, the third in 1993-95, and the fourth and last examination in 1996-98. Medical data included systolic and diastolic blood pressure, anti-hypertensive medication use, current/former smoking, diabetes, body mass index and a blood sample. Additional details regarding the study are provided in Agarwal et al., 2012, *Circ Heart Fail.* 5(4): 422-29.

The term "clinical model score" refers to any value corresponding to the risk for HF in a subject. In some embodiments, the value is a number, quantity, or curve. In some embodiments, the clinical model score is generated by one of the clinically based tools available to physicians. In certain embodiments, the clinical model score is provided by, for example, the Health ABC HF risk score, Framingham HF risk score, or the ARIC HF score. The clinical model score of a patient can also be acquired from patient information sources, such as patient record databases, medical histories, or any similar archive that may not necessarily be in a clinical setting. Clinical model scores can therefore also be generated using historical or published patient data. The clinical model score can be generated using patient data from any source, using any known tool or model that can accurately predict HF risk in a patient, and is not intended to be limited to the exemplary embodiments described herein.

The term "troponin" refers to all troponin isoforms. These isoforms are well characterized in the art, and are described in, for example, Anderson et al., 1995, *Circ. Res.* 76(4): 681-86, and Ferrieres et al., 1998, *Clin. Chem.* 44(3): 487-93. In the disclosed methods, troponin may refer to troponin T ("TnT") and/or troponin I ("TnI"). Accordingly, both troponins may be determined in the method of the present disclosure together, i.e., simultaneously or sequentially, or individually, i.e., without determining the other isoform at all. The term "troponin" encompasses also variants of the aforementioned specific troponins, i.e., troponin T or troponin I, including cardiac troponin T ("cTnT"). Amino acid sequences for human troponin T and human troponin I are described in Anderson et al., 1995 and Ferrieres et al., 1998. These documents are herewith incorporated by reference with respect to the specific sequences of troponin T ("TnT") and/or troponin I ("TnI") and variants thereof disclosed therein. TnT, which is a part of the contractile apparatus of cardiomyocytes, has been used previously as a biomarker of myocardial necrosis or damage. Low levels of circulating cardiac troponin T ("cTnT") can be measured with a highly sensitive assay, for example Elecsys® Troponin T hs (Roche Diagnostics).

The term "NT-pro B-type natriuretic peptide" or "NT-proBNP" refers to the N-terminal prohormone of brain natriuretic peptide (NT-proBNP), a 76 amino acid N-terminal fragment of brain natriuretic peptide. The structures of the human BNP and NT-proBNP have been described in detail in, e.g., International Publication Nos. WO 02/089657 and WO 02/083913. In some embodiments, human NT-proBNP as used herein is human NT-proBNP as disclosed in European Patent No. EP 0 648 228 B1. These documents are herewith incorporated by reference with respect to the specific sequences of NT-proBNP and variants thereof disclosed therein.

Levels of NT-pro B-type natriuretic peptide (NT-proBNP), a biomarker of neurohormonal activation and hemodynamic stress, have been correlated with incident HF among adults without previously recognized cardiovascular disease. NT-proBNP levels in the blood have been linked to acute congestive HF and its presence is indicative of patients with worse outcomes (Bhalla et al., 2004, *Congest Heart Fail.* 10 (1 Suppl 1): 3-27). The plasma concentrations of NT-proBNP are also typically increased in patients with asymptomatic or symptomatic left ventricular dysfunction and are associated with coronary artery disease and myocardial ischemia.

The term "natriuretic peptide" comprises Atrial Natriuretic Peptide (ANP)-type and Brain Natriuretic Peptide (BNP)-type peptides and variants thereof having the same predictive potential. Natriuretic peptides according to the present disclosure comprise ANP-type and BNP-type peptides and variants thereof (see, e.g., Bonow, 1996, *Circulation* 93(11): 1946-50). ANP-type peptides comprise pre-proANP, proANP, NT-proANP, and ANP. BNP-type peptides comprise pre-proBNP, proBNP, NT-proBNP, and BNP. The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP, 28 amino acids in the case of ANP). Suitable natriuretic peptides for use in the disclosed methods include NT-proANP, ANP, NT-proBNP, BNP, and variants thereof. ANP and BNP are the active hormones and have a shorter half-life than their respective inactive counterparts, NT-proANP and NT-proBNP. BNP is metabolized in the blood, whereas NT-proBNP circulates in the blood as an intact molecule and as such is eliminated renally. The in vivo half-life of NT-proBNP is 120 minutes longer than that of BNP, which has a half-life of only 20 minutes (Smith et al., 2000, *J. Endocrinol.* 167(2): 239-46). Preanalytics are more robust with NT-proBNP allowing easy transportation of the sample to a central laboratory (Mueller et al., 2004, *Clin. Chem. Lab. Med.* 42(8): 942-44). Blood samples can be stored at room temperature for several days or may be mailed or shipped without recovery loss. In contrast, storage of BNP for 48 hours at room temperature or at 4° Celsius leads to a concentration loss of at least 20 percent (Mueller et al., 2004; Wu et al., 2004, *Clin. Chem.* 50(5): 867-73). Therefore, depending on the time-course or properties of interest, measurement of either the active or inactive forms of the natriuretic peptide can be advantageous. In certain embodiments, the natriuretic peptides are NT-proBNP or variants thereof.

TnT or NT-proBNP may provide independent prognostic information with regard to incident HF, but the extent to which they improve risk prediction beyond clinically validated risk assessment tools, such as the ARIC HF model, is unclear. In one embodiment disclosed herein, novel HF risk prediction methods and models are generated to evaluate the impact and possible value of determining the levels of certain biomarker levels when diagnosing HF risk. Models were generated that take into account various combinations of model factors, patient variables, and biomarkers. The models, model factors, patient variables, and biomarkers associated with each model are further described in the tables disclosed herein.

Comparisons of these models for their ability to improve HF risk prediction were tested using statistical measures of discrimination and calibration, as shown in summary form in Table A, and further described in detail in Tables 4 and 5 and the Examples below.

In one embodiment, methods for diagnosing HF risk in a subject are disclosed herein. In certain embodiments, an expansion on the ARIC model is disclosed, wherein incorporating biomarker data into the HF risk calculation significantly improves HF risk prediction. For a summary of these results, see Table A: Model 1 versus Model 2. In one embodiment, the accuracy of HF risk prediction can be significantly improved by combining troponin (i.e., cTnT) and NT-proBNP data with a clinical HF risk score from the ARIC model. In certain embodiments, the biomarker data is the quantity of biomarker in a patient sample.

Table 4, showing data in detail below, compares the accuracy of each model as biomarker data is incorporated into the HF risk prediction. Accuracy is measured by differences in area under curve (AUC), net reclassification indices (NRI), and integrated discrimination indices (IDI), which were all calculated with methods that accounted for censoring (Nambi, et al., 2010, *J. Am Coll Cardiol.* 55(15): 1600-7). The incorporation of either cTnT or NT-proBNP data into the ARIC HF model increased the accuracy of the HF prediction in both men and women, as shown by AUC and NRI scores (Table 4). Moreover, the incorporation of both cTnT and NT-proBNP data resulted in an even more striking and unexpected increase in prediction accuracy (Tables 4 and 5). In a particular embodiment, biomarkers such as cTnT and NT-proBNP provide a cumulative or synergistic increase in the accuracy of the HF risk prediction.

The incorporation of both cTnT and NT-proBNP to the ARIC HF model clearly resulted in the best statistical HF risk prediction model. See, e.g., Table A: Model 1 versus Model 2. Surprisingly, this optimized model improved the accuracy of risk prediction to rival other highly accurate tests in coronary heart disease (Polonsky, et al., 2010, *JAMA.* 303(16): 1610-6.) These results indicate that the integration of biomarker data into HF prediction models significantly improves the predictive ability of that model. Integration of biomarker data can therefore be incorporated into currently accepted HF prediction models to produce an improved HF prediction model. This improved HF prediction model can be used to generate more accurate clinical HF risk scores for patient subjects.

While improved accuracy of HF risk prediction is always a major goal of medical diagnostic models for predicting HF risk, also desirable are alternative models that avoid the limitations of certain clinical HF risk predictions. Clinical risk scores, such as for example the ARIC score, require a significant amount of physician time before a risk score can be generated for a patient. Most clinical risk scores require the physician to collect a substantial list of patient variables or risk factors before a clinical risk score can be generated. For example, the clinical factors required to generate the ARIC score are shown in Tables 1 and 4. Indeed, lack of time is one major reason for the poor adaptation of clinical risk scores by physicians in their practices (Mosca et al. 2005, *Circulation.* 111(4): 499-510). Given these difficulties in the implementation of risk scores in clinical practice, a simplified yet comparable approach would certainly be used more frequently for HF risk prediction in clinical practice. However, previous tests that are able to generate heart failure risk scores faster are either not available or have unacceptable accuracy.

In another aspect, disclosed herein are novel HF risk prediction methods and models that can accurately diagnose heart failure risk in a subject using simplified model factors. Unexpectedly, the integration of biomarker quantity data with a subset of patient variables provided for a simplified model with comparable accuracy to the full ARIC clinical model.

The term "simplified model factors" refers to a set of patient data variables that are sufficient to accurately predict the risk of HF in a patient. In other embodiments, simplified model factors include any combination of one or more variables required to calculate HF risk using a clinical model score. In other embodiments, simplified model factors are selected from one or more component variables of the any HF risk model, including the following non-exhaustive examples: the ARIC model, the Health ABC model, the Framingham HF risk model, and/or the AHA staging model discussed above. In yet other embodiments, simplified model factors can include one or more of the following non-exhaustive examples: age, race, gender, systolic blood pressure, diastolic blood pressure, anti-hypertensive medication use, current/former smoking, diabetes, body mass index (BMI), prevalent coronary heart disease, and heart rate. In one embodiment, the simplified model factors are age, race, and gender. In another embodiment, the simplified model factors are age and race. In certain embodiments, a patient population is defined first by one or more patient variables before applying the HF risk model. For example, in one embodiment, gender-specific models can be used to evaluate HF risk as described. Defining the patient population prior to modelling may be required because patient variables are known to interact with other patient variables, leading to skewed data and less prediction accuracy.

Table A, shown below, presents a summary of the comparative testing between the models disclosed herein. In order for a simplified model to have clinical value, the accuracy of the simplified model must be comparable to the ARIC HF model (Model 1; Table A). Briefly, a simplified "lab model" that incorporated only age, race, gender, and certain biomarkers (Model 3; Table A), was tested against the full ARIC HF model without any biomarkers (Model 1; Table A). In one specific embodiment, the addition of biomarker data allows the lab model to predict HF with comparable accuracy as the full ARIC HF model, yet the lab model only requires a small set of easily obtained simplified model factors: age, race, and gender. As shown in greater detail in Table 5 and FIGS. 1-2, the lab model predicted HF risk with comparable accuracy to the ARIC HF model without any biomarkers. The full ARIC HF model with biomarker data (Model 2: ARIC+cTnT+NTproBNP; Table A) predicted HF with the highest accuracy.

TABLE A

Summary of Heart Failure Risk Prediction Accuracy for Selected Models

|  | Model 1 versus Model 2 | | Model 1 versus Model 3 | |
| --- | --- | --- | --- | --- |
|  | Model 1 | Model 2 | Model 1 | Model 3 |
| AUC | 0.773 | 0.818 | 0.773 | 0.774 |
| (95% CI) | (0.761, 0.788) | (0.807, 0.832) | (0.761, 0.788) | (0.760, 0.791) |
| AUC difference |  | 0.044 |  | 0.001 |
| (95% CI) |  | (0.036, 0.055) |  | (−0.013, 0.016) |
| NRI |  | 21.0 |  | −4.1 |
| (95% CI) |  | (15.9, 26.6) |  | (−11.1, 3.4) |
| Continuous NRI |  | 47.9 |  | −5.9 |
| (95% CI) |  | (39.8, 56.9) |  | (−17.1, 6.3) |
| IDI |  | 0.085 |  | 0.017 |
| (95% CI) |  | (0.069, 0.104) |  | (−0.004, 0.039) |
| GB statistic | 39.4 | 23.7 | 39.4 | 7.8 |
| (p-value) | (<0.0001) | (0.005) | (<0.0001) | (0.55) |

CI: confidence interval; AUC: Area under the receiver operator characteristics curve; NRI: net reclassification index; IDI: integrated discrimination index; GB statistic; Groonesby Borgan goodness of fit test for model calibration
Model 1: age, race, gender, systolic blood pressure, antihypertensive medication use, current smoking, diabetes, body mass index, prevalent coronary heart disease and heart rate; Model 2: Model 1 + TnT + NT-proBNP; Model 3: age, race, gender, TnT, NT-proBNP
Troponin catergories: undetectable, 0.003-0.005 µg/L, 0.006-0.008 µg/L, 0.009-0.013 µg/L, ≥0.014 µg/L As disclosed herein, the incorporation of biomarker data into clinical HF prediction models can improve prediction accuracy such that many of the patient variable components of the clinical HF model may be omitted without significant loss of prediction accuracy. Furthermore, as shown in one embodiment, many of the more time-consuming and/or labor intensive patient variables can be eliminated without loss of prediction accuracy. This unexpected result confirms that collection of biomarker data from a patient sample can be used as a substitute for a large subset of patient variables.

By way of example only, the lab model disclosed herein does not require a physician to determine the diabetic status of the patient to achieve prediction accuracy that is comparable to the clinical HF models. By eliminating the need to immediately determine whether a patient is diabetic, which may require significant time to send out and return patient samples from a third-party laboratory, a patient can instead be diagnosed with HF risk much earlier using the lab model. Furthermore, such as in the specific example of simplified model factors age, race, and gender, these patient variables can be obtained by a non-physician staff member if a physician is not available, also allowing for significantly faster HF risk results. Eliminating the step of obtaining other labor-intensive patient variables such as, for example, body mass index, systolic blood pressure, diastolic blood pressure, or heart rate provides for a much more efficient prediction model for HF. This more efficient model for predicting HF would yield, for example, reductions in cost, time, and training, and would therefore be expected to increase physician adoption in practice.

In certain embodiments, the method for diagnosing HF risk disclosed herein may be automated. In one embodiment, provision of actuarial risk estimates for HF would be simplified based on the disclosed lab model, and could be implemented automatically as is currently done in most institutions for estimation of glomerular filtration rate (eGFR) (Johnson et al., 2012, *Med. J. Aust.* 197(4): 224-5). Indeed, when eGFR (along with various cut-points) reporting was required with each measurement of serum creatinine, several reports suggested a beneficial positive impact in clinical practice (Cortes-Sanabria L. et al., 2008, *Am. J. Kidney Dis.* 51(5): 777-88). Automatic implementation of a simplified model could produce an improvement in clinical practice with HF risk prediction, which would represent a significant improvement to public health.

Practicing clinicians often struggle with determining which individuals having patient variable risk factors for HF (such as, for example, hypertension) to subject to further imaging or testing. In one embodiment, the lab model for HF risk allows a physician to identify individuals at high risk for HF based on a lab test or risk score, which can inform the decision on whether to obtain an imaging test such as an echocardiogram. Therefore, the methods disclosed herein will help the clinician in appropriately referring only a limited number of individuals for additional testing.

Furthermore, early detection of HF risk could lead to change in behavior and mediation of risk factors, including primordial prevention (preventing the development of risk factors) which is associated with marked decreases in the incidence of various CVD including HF (Folsom, et al., 2009, *Circ. Heart Fail*, 2(1): 11-7.) and should clearly be the focus of future efforts in reducing HF.

Also contemplated in some embodiments is the generation of a simplified HF risk score, which would represent a patient's HF risk according to the specific lab model used. The simplified HF risk score can be a single numerical value, a curve, a series of values, quantification of change, or any other representative quantity. This simplified HF risk score can be compared to any number of model scores, controls, model curves, published or clinically-derived threshold values, and any other diagnostic value as may be apparent to one of ordinary skill in the art. Comparison of the simplified HF risk score with accurate clinical HF risk scores is but one example of a means to determine the accuracy of a particular simplified lab model. The comparison of quantities, scores, or curves with one or more other results is well known in the field of statistics. The comparison of a simplified HF risk score with either the clinical HF risk score or some other threshold value is but one example of a method of determining HF risk in a patient, and should not be read as limiting to the instant disclosure.

In another aspect, the methods and models disclosed herein can be used to inform the design of clinical trials. In one example, the lab model can be used to quickly generate HF risk scores for a set of patients eligible for clinical trials. The risk scores may be used to identify the highest risk individuals who clearly are the patients most likely to benefit from the drug, device, biologic, and/or other medical intervention being studied. In another embodiment, simplified model factors are identified for a particular study and then data sources are expanded to encompass historical data or preserved samples. For example, if a viable patient sample exists to test for biomarkers, the HF risk of the patient can be predicted based only on the patient's age, race, and gender. In contrast, the ARIC model cannot be applied accurately to preserved samples unless all of the required patient variables are recorded and stored with the sample.

In yet another aspect of the disclosed methods, the predicted risk of HF is negligible when the amount of troponin in a patient sample is undetectable. As disclosed herein, when cTnT was assessed (Table 6), almost all individuals who developed HF had a detectable concentration of cTnT. This result suggests that an undetectable cTnT level has a high negative predictive value. Using any of the models disclosed herein, obtaining an undetectable cTnT level from a patient sample can be used to predict negligible HF risk for the patient.

The terms "NT-proBNP," "natriuretic peptide," and "troponin," as used herein, also encompass variants of the aforementioned specific polypeptides. Such variants have at least the same essential biological and immunological properties as the specific polypeptide of the present disclosure. In particular, they share the same essential biological and immunological properties if they are detectable by the same specific assays referred to in this specification, e.g., by ELISA assays using polyclonal or monoclonal antibodies specifically recognizing said polypeptides. Moreover, it is to be understood that a variant as referred to in the present disclosure shall have an amino acid sequence having at least one amino acid substitution, deletion, and/or addition wherein the amino acid sequence of the variant is still at least about 50%, at least about 60%, at least about 70%, at least about 80%, at least about 85%, at least about 90%, at least about 92%, at least about 95%, at least about 97%, at least about 98%, or at least about 99% identical to the amino acid sequence of the polypeptide of the present disclosure, over the entire length of the peptide. In the context of sequence identity of amino acid sequences or nucleic acid sequences, the term "at least about" refers to a sequence identity exceeding the indicated exact numerical value. The degree of identity between two amino acid sequences can be determined by algorithms well known in the art. In certain embodiments, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison, and multiplying the result by 100 to yield the percentage of sequence identity. Optimal alignment of sequences for comparison may be conducted by the local homology algorithm of Smith and Waterman, 1981, *Adv. Appl. Math.* 2: 482-89, by the homology alignment algorithm of Needleman and Wunsch, 1970, *J. Mol. Biol.* 48(3): 443-53, by the search for similarity method of Pearson and Lipman, 1988, *PNAS U.S.A.* 85(8): 2444-48, by computerized implementations of these algorithms (GAP, BESTFIT, BLAST, PASTA, and TFASTA in the Wisconsin Genetics Software Package, Genetics Computer Group (GCG), Madison, Wis.), or by visual inspection. Given that two sequences have been identified for comparison, GAP and BESTFIT may be employed to determine their optimal alignment and, thus, the degree of identity. In one embodiment, the default values of 5.00 for gap weight and 0.30 for gap weight length are used. Variants referred to above may be allelic variants or any other species-specific homologs, paralogs, or orthologs. Moreover, the variants referred to herein include fragments or subunits of the specific polypeptide or the aforementioned types of variants as long as these fragments have the essential immunological properties and/or biological activities as referred to above. Such fragments may be, e.g., degradation products of the polypeptides of the present disclosure. Also included are variants that differ due to posttranslational modifications such as phosphorylation or myristylation.

Determining the amount of NT-proBNP, a natriuretic peptide, troponin, or any other peptide or polypeptide referred to in this specification relates to measuring the amount or concentration. In certain embodiments, such measurements are semi-quantitative or quantitative. Measuring can be done directly or indirectly. Direct measuring relates to measuring the amount or concentration of the peptide or polypeptide based on a signal which is obtained from the peptide or polypeptide itself and the intensity of which directly correlates with the number of molecules of the peptide present in the sample. Such a signal—sometimes referred to herein as intensity signal—may be obtained, for example, by measuring an intensity value of a specific physical or chemical property of the peptide or polypeptide. Indirect measuring includes measuring of a signal obtained from a secondary component (i.e., a component not being the peptide or polypeptide itself) or a biological read out system, e.g., measurable cellular responses, ligands, labels, or enzymatic reaction products.

In accordance with the present disclosure, determining the amount of a peptide or polypeptide can be achieved by all known means for determining the amount of a peptide in a sample. Said means comprise immunoassay devices and methods that may utilize labelled molecules in various sandwich, competition, or other assay formats. Said assays will develop a signal which is indicative for the presence or absence of the peptide or polypeptide. Moreover, the signal strength can be correlated directly or indirectly (e.g., reverse-proportional) to the amount of polypeptide present in a sample. Other suitable methods comprise measuring a physical or chemical property specific for the peptide or polypeptide such as its precise molecular mass or NMR spectrum. Said methods may comprise biosensors, optical devices coupled to immunoassays, biochips, and analytical devices such as mass-spectrometers, NMR-analyzers, or chromatography devices. Other suitable methods include micro-plate ELISA-based methods, fully-automated or robotic immunoassays (available, for example, on Roche ELECSYS™ and Cobas® analyzers, for instance the Cobas® 4000 and Cobas® 6000 analyzer series, and the Cobas® 8000 modular analyser series, which are well-known in the art), CBA (an enzymatic Cobalt Binding Assay, available, for example, on ROCHE-HITACHI™ analyzers), and latex agglutination assays (available, for example, on ROCHE-HITACHI™ analyzers).

In one embodiment of the methods of the disclosure, the amount of a peptide or polypeptide is determined by contacting a cell capable of eliciting a cellular response, wherein the intensity is indicative of the amount of the peptide or polypeptide, with said peptide or polypeptide for an adequate period of time, and measuring the cellular response. For measuring cellular responses, the sample or processed sample can be added to a cell culture and an internal or external cellular response is measured. The cellular response may include the measurable expression of a reporter gene or the secretion of a substance, e.g., a peptide, polypeptide, or a small molecule. The expression or substance shall generate an intensity signal that correlates to the amount of the peptide or polypeptide.

In another embodiment of the methods of the disclosure, the amount of a peptide or polypeptide is determined by measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

In another embodiment of the methods of the disclosure, the amount of a peptide or polypeptide is determined by contacting the peptide with a specific ligand, optionally removing non-bound ligand, and measuring the amount of bound ligand. The bound ligand will generate an intensity signal. Binding according to the present disclosure includes both covalent and non-covalent binding. A ligand according to the present disclosure can be any compound, e.g., a peptide, polypeptide, nucleic acid, or small molecule, binding to the peptide or polypeptide described herein. Suitable ligands include antibodies, nucleic acids, peptides or polypeptides such as receptors or binding partners for the peptide or polypeptide and fragments thereof comprising the binding domains for the peptides, and aptamers, e.g., nucleic acid or peptide aptamers. Methods to prepare such ligands are well known in the art. For example, identification and production of suitable antibodies or aptamers is offered by commercial suppliers. Those skilled in the art are familiar with methods to develop derivatives of such ligands with higher affinity or specificity. For example, random mutations can be introduced into the nucleic acids, peptides, or polypeptides. These derivatives can then be tested for binding according to screening procedures known in the art, e.g., phage display. Antibodies as referred to herein include both polyclonal and monoclonal antibodies, as well as fragments thereof, such as Fv, Fab and $F(ab)_2$ fragments that are capable of binding antigen or hapten. The present disclosure also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. In some embodiments, the ligand or agent specifically binds to the peptide or polypeptide. Specific binding according to the present disclosure means that the ligand or agent should not bind substantially to ("cross-react" with) another peptide, polypeptide, or substance present in the sample to be analyzed. In certain embodiments, the specifically bound peptide or polypeptide should be bound with at least 3 times higher, at least 10 times higher, or at least 50 times higher affinity than any other relevant peptide or polypeptide. Non-specific binding may be tolerable if it can still be distinguished and measured unequivocally, e.g., according to its size on a Western Blot, or by its relatively higher abundance in the sample. Binding of the ligand can be measured by any method known in the art. In certain embodiments, the method is semi-quantitative or quantitative. Suitable methods are described herein.

First, binding of a ligand may be measured directly, e.g., by NMR or surface plasmon resonance.

Second, if the ligand also serves as a substrate of an enzymatic activity of the peptide or polypeptide of interest, an enzymatic reaction product may be measured (e.g., the amount of a protease can be measured by measuring the amount of cleaved substrate, e.g., on a Western Blot). Alternatively, the ligand may exhibit enzymatic properties itself and the "ligand/peptide or polypeptide" complex or the ligand which was bound by the peptide or polypeptide, respectively, may be contacted with a suitable substrate allowing detection by the generation of an intensity signal.

For measurement of enzymatic reaction products, the amount of substrate can be saturating. The substrate may also be labelled with a detectable label prior to the reaction. In one embodiment, the sample is contacted with the substrate for an adequate period of time. An adequate period of time refers to the time necessary for a detectable and measurable amount of product to be produced. Instead of measuring the amount of product, the time necessary for appearance of a given (e.g., detectable) amount of product can be measured.

Third, the ligand may be coupled covalently or non-covalently to a label allowing detection and measurement of the ligand. Labelling may be done by direct or indirect methods. Direct labelling involves coupling of the label directly (covalently or non-covalently) to the ligand. Indirect labelling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. Secondary, tertiary, or even higher order ligands are often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-Tag, Glutathione-S-transferase, FLAG, GFP, myc-tag, influenza A virus hemagglutinin (HA), maltose binding protein, and the like. In the case of a peptide or polypeptide, the tag may be located at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels (e.g., magnetic beads, including paramagnetic and superparamagnetic labels), and fluorescent labels. Enzymatically active labels include e.g., horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-STAR™ (Amersham Biosciences), ECF™ (Amersham Biosciences). A suitable enzyme-substrate combination may result in a colored reaction product, fluorescence, or chemoluminescence, which can be measured according to methods known in the art (e.g., using a light-sensitive film or a suitable camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g., Alexa 568). Other fluorescent labels are available e.g., from Molecular Probes (Oregon). Also the use of quantum dots as fluorescent labels is contemplated. Typical radioactive labels include $^{35}S$, $^{125}I$, $^{32}P$, $^{33}P$, and the like. A radioactive label can be detected by any method known and appropriate, e.g., a light-sensitive film or a phosphor imager. Suitable measurement methods according the present disclosure also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), turbidimetry, nephelometry, latex-enhanced turbidimetry or nephelometry, or solid phase immune tests. Other methods known in the art (such as gel electrophoresis, 2D gel electrophoresis, SDS polyacrylamide gel electrophoresis (SDS-PAGE), Western Blotting, and mass spectrometry) can be used alone or in combination with labelling or other detection methods as described above.

The amount of a peptide or polypeptide may also be determined by contacting a solid support comprising a ligand for the peptide or polypeptide as specified above with a sample comprising the peptide or polypeptide and measuring the amount peptide or polypeptide which is bound to the support. The ligand may be chosen from the group consisting of nucleic acids, peptides, polypeptides, antibodies and aptamers, and can be present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, and plastic tubes. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the disclosure. Suitable methods for fixing/immobilizing said ligand are well known and include, but are not limited to ionic, hydrophobic, covalent interactions and the like. It is also contemplated to use "suspension arrays" as arrays according to the present disclosure (Nolan et al., 2002, *Trends Biotechnol.* 20(1): 9-12). In such suspension arrays, the carrier, e.g., a microbead or microsphere, is present in suspension. The array consists of different microbeads or microspheres, possibly labelled, carrying different ligands. Methods of producing such arrays, for example based on solid-phase chemistry and photo-labile protective groups, are generally known (U.S. Pat. No. 5,744,305).

The term "sample" refers to a sample of a body fluid, to a sample of separated cells or to a sample from a tissue or an organ. Samples of body fluids can be obtained by well known techniques and include, for example, samples of blood, plasma, serum, or urine. In certain embodiments of the disclosed methods, the sample is blood, plasma, or serum. Tissue or organ samples may be obtained from any tissue or organ by, e.g., biopsy. Separated cells may be obtained from the body fluids or the tissues or organs by separating techniques such as centrifugation or cell sorting. In some embodiments, cell, tissue, or organ samples are obtained from those cells, tissues, or organs that express or produce the peptides referred to herein.

The term "comparing" as used herein encompasses comparing the amount of the peptide or polypeptide comprised by the sample to be analyzed with an amount of a suitable reference source specified elsewhere in this description. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample. A comparison may be carried out manually or with the assistance of a computer. For a computer assisted comparison, the value of the determined amount may be compared to values corresponding to suitable references which are stored in a database by a computer program. The computer program may further evaluate the result of the comparison, i.e., automatically provide the desired assessment in a suitable output format. Based on the comparison of the amounts determined in step a) and the reference amount of the method of the present disclosure, it is possible to predict the risk of the patient suffering from one or more of the complications referred to herein. Therefore, the reference amount is to be chosen so that either a difference or a similarity in the compared amounts allows identifying those patients who are at risk of heart failure.

Accordingly, the term "reference amount" as used herein refers to an amount that allows predicting whether a patient has an increased risk of heart failure. The reference amount may define a threshold amount, whereby an amount larger than the threshold shall be indicative for a subject that is at increased risk of HF. The reference amount applicable for an individual subject may vary depending on various physiological parameters such as age, gender, or subpopulation, as well as on the means used for the determination of the polypeptide or peptide referred to herein. A suitable reference amount may be determined by the method of the present disclosure from a reference sample to be analyzed together, i.e., simultaneously or subsequently, with the test sample. In certain embodiments, the reference amount serving as a threshold may be derived from the upper limit of normal (ULN), for example the upper limit of the physiological amount to be found in samples from a population of subjects with no incidence of HF and/or minimal HF risk. The ULN for a given population of subjects can be determined by various well-known techniques. A suitable technique may be to determine the median or average of the population for the peptide or polypeptide amounts to be determined in the method of the present disclosure. Non-limiting examples of suitable reference amounts are described herein.

Reference amounts of a diagnostic marker (i.e., of NT-proBNP, a natriuretic peptide and/or troponin) can be established, and the level of the marker in a patient sample can simply be compared to the reference amount. The sensitivity and specificity of a diagnostic and/or prognostic test depends on more than just the analytical "quality" of the test—they also depend on the definition of what constitutes an abnormal result.

Statistical methods well known to the person skilled in the art can be used to define a threshold amount that can be used to separate patients at risk and patients not at risk. A suitable statistical method for this purpose is the calculation of Receiver Operating Characteristic curves, or "ROC" curves. ROC-curves are typically calculated by plotting the value of a variable versus its relative frequency in "normal" and "disease" populations. For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold may be selected above which (or below which, depending on how a marker changes with the disease) the test is considered to be abnormal and below which the test is considered to be normal. The area under the ROC curve is a measure of the probability that the perceived measurement will allow correct identification of a condition. For further information, see Dowdy and Wearden, *Statistics for Research* (John Wiley & Sons, New York 1983). ROC curves can be used even when test results do not necessarily give an accurate number. As long as one can rank results, one can create an ROC curve. For example, results of a test on "disease" samples might be ranked according to degree (say 1=low, 2=normal, and 3=high). This ranking can be correlated to results in the "normal" population, and a ROC curve created. These methods are well known in the art. See, e.g., Hanley et al., 1982, *Radiology* 143(1): 29-36.

In certain embodiments, markers (i.e., NT-proBNP, a natriuretic peptide, and/or troponin) are selected to exhibit at least about 70% sensitivity, or at least about 80% sensitivity, or at least about 85% sensitivity, or at least about 90% sensitivity, or at least about 95% sensitivity, combined with at least about 70% specificity, or at least about 80% specificity, or at least about 85% specificity, or at least about 90% specificity, or at least about 95% specificity. In certain embodiments, both the sensitivity and specificity are at least about 75%, or at least about 80%, or at least about 85%, or at least about 90%, or at least about 95%.

The term "about" is meant to indicate +/−30% of the indicated amount, or +/−20% of the indicated amount, or +/−10% of the indicated amount, or +/−5% of the indicated amount.

The term "detection agent," as used herein, refers to an agent that is capable of specifically recognizing and binding to one of the biomarkers referred to herein when present in a sample. Moreover, the detection agent shall allow for direct or indirect detection of the complex formed by the detection agent and the biomarker. Direct detection can be achieved by incorporating a detectable label in the detection agent. Indirect labelling may be achieved by using a second agent that specifically binds to a complex comprising the biomarker and the detection agent, wherein the second agent is than capable of generating a detectable signal. Suitable compounds for use as detection agents are well known in the art. In some embodiments of the disclosed methods, the detection agent is an antibody (e.g., a monoclonal or a polyclonal antibody) or aptamer that specifically binds to the biomarker.

Furthermore, the present disclosure relates to a device for predicting the risk of HF in a patient. In one embodiment, the device comprises an analyzing unit for determining the amount of NT-proBNP and/or troponin in a sample obtained from the patient; and an evaluation unit for comparing the determined amount with a suitable reference amount and for predicting the risk of HF. In other embodiments, the device comprises alternative components.

The term "device" as used herein relates to a system comprising at least the aforementioned means operatively linked to each other as to practice the method of the present disclosure. Suitable means for determining the amounts of the markers of the disclosed methods, and means for carrying out the comparison are disclosed above in connection with the disclosed methods. How to link the means in an operating manner will depend on the type of means included in the device. For example, where an analysis unit for automatically determining the amount of the gene products of the present disclosure is applied, the data obtained by said automatically operating analysis unit can be processed by, e.g., a computer as evaluation unit in order to obtain the desired results. In some embodiments, the means are comprised of a single device in such a case.

In some embodiments, the device for predicting the risk of HF in an at-risk patient includes an analyzing unit for the measurement of the amount of NT-proBNP and/or troponin in an applied sample and an evaluation unit for processing the resulting data. In certain embodiments, the evaluation unit comprises a database with the stored reference amounts and a computer program code which when tangibly embedded on a computer carries out the comparison of the determined amounts and the reference amounts stored in the database. In other embodiments, the evaluation unit comprises a further computer program code that allocates the result of the comparison to a risk prediction. In such a case, it is envisaged that the evaluation unit comprises a further database wherein the reference amounts are allocated to the risks.

Alternatively, where means such as test strips are used for determining the amount of NT-proBNP and/or troponin, the evaluation unit may comprise control strips or tables allocating the determined amount to a reference amount. In some embodiments, the test strips are coupled to ligands that specifically bind to NT-proBNP and/or troponin. In other embodiments, the strip or device comprises means for detection of the binding of NT-proBNP and/or troponin to said ligands. Suitable means for detection are disclosed in connection with embodiments relating to the disclosed methods. In such a case, the analysis unit and the evaluation unit are operatively linked in that the user of the system brings together the result of the determination of the amount and the diagnostic or prognostic value thereof due to the instructions and interpretations given in a manual. The analysis unit and the evaluation unit may appear as separate devices in such an embodiment, and in some embodiments are packaged together as a kit. A person skilled in the art will realize how to link the means. Suitable devices are those that can be applied without the particular knowledge of a specialized clinician, e.g., test strips or electronic devices that merely require loading with a sample. The results may be given as output of raw data, which need interpretation by the clinician. In certain embodiments, however, the output of the device is processed, i.e., evaluated, raw data that does not require interpretation by a clinician. Other suitable devices comprise the analyzing units/devices (e.g., biosensors, arrays, solid supports coupled to ligands specifically recognizing the gene product, plasmon surface resonance devices, NMR spectrometers, or mass-spectrometers) or evaluation units/devices referred to above in accordance with the methods of the disclosure.

Moreover, the present disclosure relates to a kit for predicting the risk of HF in a patient, comprising an analyzing agent for determining the amount of NT-proBNP and/or troponin in a sample obtained from the patient; and an evaluation unit for comparing the amounts determined by the analyzing agent with a suitable reference amount, said unit further allowing the prediction of the risk of heart failure.

The term "kit" as used herein refers to a collection of the aforementioned components that may or may not be packaged together. The components of the kit may be comprised by separate vials (i.e., as a kit of separate parts) or provided in a single vial. Moreover, it is to be understood that the kit of the present disclosure is to be used for practicing the methods referred to herein. In some embodiments, it is envisaged that all components are provided in a ready-to-use manner for practicing the methods referred to above. In certain embodiments, the kit also contains instructions for carrying out the disclosed methods. The instructions can be provided by a user's manual in paper or electronic form. For example, the manual may comprise instructions for interpreting the results obtained when carrying out the aforementioned methods using the kit of the present disclosure. The kit shall comprise an analyzing agent. This agent is capable of specifically recognizing NT-proBNP and/or troponin in a sample obtained from the patient. Moreover, in some embodiments, the agent(s) shall, upon binding to the NT-proBNP and/or troponin, be capable of generating a detectable signal, the intensity of which correlates to the amount of NT-proBNP and/or troponin present in the sample. Depending on the type of signal that is generated, methods for detection of the signal can be applied which are well known in the art. Analyzing agents that can be used for the kit of the present disclosure include antibodies or aptamers. The analyzing agent may be present on a test strip as described herein. The amounts of NT-proBNP and/or troponin detected can then be further evaluated in the evaluation unit. Suitable evaluation units to be used for the kit of the present disclosure include those referred to herein.

All publications, patents, and applications are hereby incorporated by reference in their entirety to the same extent as if each such reference was specifically and individually indicated to be incorporated by reference in its entirety.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

One embodiment of the disclosure is directed to a method for diagnosing heart failure risk in a subject, comprising: a) obtaining the subject's simplified model factors; b) obtaining the amount of Troponin T (TnT) and NT-pro B-type natriuretic peptide (NT-proBNP) in a biological sample obtained from the subject; c) obtaining a simplified model score based on the amount of TnT and NT-proBNP in the biological sample obtained from the subject and the subject's simplified model factors; d) obtaining the alignment value of the simplified model score compared to a clinical model score; and e) providing a diagnosis of heart failure risk if the alignment value exceeds a threshold.

Another embodiment of the disclosure is directed to a method for identifying a subject as in need of therapy for heart failure, comprising: a) obtaining the subject's simplified model factors; b) contacting a portion of a biological sample obtained from the subject with an antibody immunoreactive for Troponin T (TnT); c) contacting a portion of the biological sample obtained from the subject with an antibody immunoreactive for a NT-pro B-type natriuretic peptide (NT-proBNP); d) determining an amount of TnT and an amount of NT-proBNP in the biological sample obtained from the subject; e) determining a simplified model score based on the amount of TnT and NT-proBNP in the biological sample obtained from the subject and the subject's simplified model factors; f) comparing the simplified model score to a clinical model score to determine an alignment value; and g) identifying the subject as in need of therapy for heart failure if the alignment value is above a threshold.

Another embodiment of the disclosure is directed to a method for facilitating a therapeutic decision in a subject, comprising: a) obtaining the subject's simplified model factors; b) contacting a first portion of a biological sample obtained from the subject with a first antibody immunoreactive for Troponin T (TnT) and contacting a second portion of the biological sample obtained from the subject with a second antibody immunoreactive for a NT-pro B-type natriuretic peptide (NT-proBNP); c) determining an amount of TnT and an amount of NT-proBNP in the biological sample obtained from the subject; d) determining a simplified model score based on the amount of TnT and NT-proBNP in the biological sample obtained from the subject and the subject's simplified model factors; and e) fitting the simplified model score/curve to a clinical model score; wherein a fit above a threshold is indicative of a need for therapy for heart failure risk.

Another embodiment of the disclosure is directed to a method of selecting a treatment for a subject with heart failure risk, comprising: a) obtaining the subject's simplified model factors; b) contacting a portion of a biological sample obtained from the subject with an antibody immunoreactive for Troponin T (TnT); c) contacting a portion of the biological sample obtained from the subject with an antibody immunoreactive for a NT-pro B-type natriuretic peptide (NT-proBNP); d) determining an amount of TnT and an amount of NT-proBNP in the biological sample obtained from the subject based on said steps of contacting; e) calculating a simplified model score based on the amount of TnT and NT-proBNP determined in said step of determining and the subject's simplified model factors; f) aligning the simplified model score to a clinical model score; and g) selecting a treatment for heart failure when the simplified model score significantly aligns to the clinical model score.

Another embodiment of the disclosure is directed to a model for predicting risk of heart failure in a subject, comprising: a) simplified model factors obtained from the subject; b) an amount of Troponin T (TnT) in a biological sample obtained from the subject; and c) an amount of NT-pro B-type natriuretic peptide (NT-proBNP) in a biological sample obtained from the subject; wherein the simplified model factors, amount of TnT, and amount of NT-proBNP are operatively combined/calculated to predict risk of heart failure in a subject.

Another embodiment of the disclosure is directed to a system/device/assay adapted for facilitating a therapeutic decision in a subject, comprising: a) means for contacting a first portion of a biological sample from the subject with a first antibody immunoreactive for Troponin T (TnT); b) means for contacting a second portion of the biological sample obtained from the subject with a second antibody immunoreactive for NT-pro B-type natriuretic peptide (NT-proBNP); c) a computing device having a processor; and d) a non-transient machine readable media including a plurality of instructions executable by the processor, the instructions, when executed, determine a simplified model score based on the amount of TnT and NT-proBNP in the biological sample obtained from the subject and the subject's simplified model factors, and provide an output indicating a need for therapy for heart failure risk in the subject if the simplified model score significantly aligns to a clinical model score.

Another embodiment of the disclosure is directed to a method of predicting a clinical heart failure risk score in a subject, comprising: a) obtaining the subject's simplified model factors; b) obtaining the amount of Troponin T (TnT) and NT-pro B-type natriuretic peptide (NT-proBNP) in a biological sample obtained from the subject; c) obtaining a simplified model score based on the amount of TnT and NT-proBNP in the biological sample obtained from the subject and the subject's simplified model factors; d) obtaining the alignment value of the simplified model score compared to a clinical model score; and e) predicting a clinical heart failure risk score if the alignment value exceeds a threshold.

Yet another embodiment of the disclosure is directed to a method of improving the prediction accuracy of a clinical heart failure risk score for a subject, comprising: a) obtaining the clinical heart failure risk score for the subject; b) obtaining an amount of Troponin T (TnT) and an amount of NT-pro B-type natriuretic peptide (NT-proBNP) in a biological sample obtained from the subject; and c) combining the amount of TnT and NT-proBNP with the clinical heart failure risk score to improve the prediction accuracy of the clinical heart failure risk score for the subject.

The following examples and figures are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It should also be understood that modifications can be made in the procedures set forth without departing from the spirit of the disclosure.

EXAMPLES

Example 1: ARIC Study Population

The study population was generated using data obtained following the fourth ARIC examination (1997-99). From the 11,656 eligible individuals, those whose race was neither Black nor White (n=31), Black participants from the Washington County, Md. or Minneapolis centers (n=38), those with prevalent HF at examination 1 (n=410), those missing HF status at examination 1 (n=199), those missing covariates for ARIC HF model (n=354), those with HF hospitalization between examination 1 and 4 (n=229), those missing covariates for ARIC HF model (n=354), cTnT values (n=365), or NT-proBNP values (n=9), and those with extreme NT-proBNP 6025 pg/ml (n=6), or not having given full consent (n=249) were excluded, leaving 9,868 individuals with adequate sample eligible for the analysis. Participants with biomarker levels below the detectable limit were assigned half the lower limit of detection. The mean age of the study population was 62.7 years; 44% were males, and ~79.5% were White. Other demographics of the study population are shown in Table 1. In all, ~46% of the subjects were hypertensive while ~16% had diabetes. Overall, ~74% had at least one of the following risk factors: diabetes, hypertension, obesity, metabolic syndrome, or prevalent cardiovascular disease that would qualify them to have at least "Stage A" heart failure, while ~26% had none of these risk factors, referred to as "Stage 0" (See, e.g., Tables 6 and 7).

TABLE 1

Baseline Characteristics (Unadjusted Means and Percentages Unless Otherwise Specified): The ARIC Study, 4$^{th}$ Examination

| Demographics | |
|---|---|
| Age (years) | 62.7 (5.65) |
| White (%) | 79.5 |
| Male (%) | 44.0 |
| Body-mass index | 28.6 (5.44) |
| Medical History | |
| Hypertension (%) | 45.7 |
| Diabetes Mellitus (%) | 15.6 |
| Systolic Blood Pressure (mm Hg) | 127.3 (18.91) |
| Diastolic Blood Pressure (mm Hg) | 71.0 (10.24) |
| Current Smoking history (%) | 14.7 |
| Former Smoking history (%) | 43.4 |
| Laboratory Data | |
| Total Cholesterol (mg/dL) | 201.4 (36.91) |
| HDL-c (mg/dL) | 50.2 (16.54) |
| Triglycerides (mg/dL) | 142.9 (86.97) |

TABLE 1-continued

Baseline Characteristics (Unadjusted Means and Percentages Unless Otherwise Specified): The ARIC Study, 4th Examination

| | |
|---|---|
| Glomerular filtration rate (eGFR; ml/min/1.73 m$^2$) | 82.3 (18.96) |
| hs-CRP, mean [median] (SD), mg/L | 4.3 [2.3] (6.44) |
| NT-proBNP, mean [median] (SD), pg/mL | 122.1 [66.7] (259.36) |
| cTnT, mean [median] (SD), ng/L | 6.5 [5.0] (17.0) |
| Medications | |
| Aspirin (%) | 56.1 |
| Antihypertensive use (%) | 34.3 |
| Statins (%) | 10.9 |
| Non-statin lipid lowering drugs (%) | 3.0 |
| Other parameters | |
| Left ventricular hypertrophy by ECG (%) | 3.0 |

Example 2. Determination of cTnT and NT-proBNP Levels of ARIC Participants

Cardiac troponin T (cTnT) and NT-proBNP levels were measured using stored blood samples collected during the fourth ARIC examination described in Example 1.

Assays: Cardiac troponin T (cTnT) was measured using a 5th Generation, highly sensitive assay (Elecsys® Troponin T hs; Roche Diagnostics, Indianapolis, Ind. U.S.A.) (Hermsen, D. et al. 2007, *Clin Lab.*, 53(1-2): 1-9). A cobas e 411 automated analyzer (Roche Diagnostics) was used to quantify the amount of cTnT. A detailed report on sources of variability, interassay reliability coefficients, repeatability of measurements and coefficients of variation in the ARIC study has been previously described (Agarwal et al., 2012, *Circ Heart Fail.* 5(4): 422-29; Saunders, A. T. et al., 2011, *Circulation.* 123(13): 1367-76). Briefly, the lower and upper limits of detection of the cTnT assay are 3 and 10,000 ng/L, respectively, and the limit of quantitation (the lowest analyte concentration that can be reproducibly measured with an intermediate-precision coefficient of variation of <10%) is 13 ng/L. The reliability coefficient and interassay coefficient of variation, based on 418 blind-replicate quality control samples before and after removal of outliers (>3 standard deviations), were 0.98 and 23.1%, and 0.99 and 15%, respectively. The interassay coefficient of variation, based on 103 runs, at cTnT levels of 29 ng/L and 2378 ng/L were 6.2% and 2.6%, respectively.

N-terminal pro B-type natriuretic peptide (NT-proBNP) was also measured on the automated cobas e 411 analyzer (Roche Diagnostics) using the Elecsys® proBNP II electrochemiluminescent immunoassay (Roche Diagnostics, Indianapolis, Ind. U.S.A.) with a measurement range of 5-35,000 pg/mL and a limit of quantitation of 35 pg/mL. The coefficient of variation for NT-proBNP has been described previously. (Bayes-Genis, A. et al., 2004, *Eur J Heart Fail.* 6(3): 301-308). The reliability coefficient and interassay coefficient of variation, based on 418 blind-replicate quality control samples before and after removal of outliers (>3 standard deviations), were 1.00 and 9.9% and 1.00 and 6.7%, respectively. The interassay coefficient of variation, based on 83 runs, at NT-proBNP levels of 121.6 pg/mL and 4059.1 pg/mL were 6.97% and 6.76%, respectively. The NT-proBNP assay is described in further detail by Agarwal et al., 2011, *Clin Chem.* 57:891-897.

Troponin was evaluated as 6-categories: undetectable, 3-5 ng/L, 6-8 ng/L, 9-13 ng/L, 14-25 ng/L, and 25 ng/L. The logarithm of NT-proBNP was used, as has been done in the previously published clinical ARIC HF model by Agarwal et al., 2012, *Circ Heart Fail.* 5(4): 422-29. Before finalizing the risk prediction models, the interactions between cTnT, NT-proBNP, and either the full ARIC patient data variables or the subset of simplified variables were tested. Interactions with gender and with some patient risk factors were found, so gender-specific models were used. When gender-specific models were used, the interactions with other variables in the risk prediction models were no longer statistically significant.

Example 3. Determination of Cox Hazard Ratios

Using Cox proportional hazards models, the hazard ratio for the association of cTnT (Table 2) and NT-proBNP (Table 3) with incident of HF was determined. Model factors were adjusted for age, race and cTnT (Table 3) or NT-proBNP (Table 2). Hazard ratios were also determined when model factors were adjusted for all components of the ARIC heart failure risk prediction model, and either cTnT (Table 3) or NT-proBNP (Table 2).

TABLE 2

Hazard Ratios for Association of Troponin T (cTnT) with Heart Failure: The ARIC Study, 4th Examination

| Troponin categories (ng/L) | Men | | Women | |
|---|---|---|---|---|
| Model Factors | Age, race, NT-proBNP | Full ARIC, NT-proBNP | Age, race, NT-proBNP | Full ARIC, NT-proBNP |
| Undetectable | 1 | 1 | 1 | 1 |
| 3 to ≤5 | 1.55 (1.00, 2.43) | 1.59 (1.02, 2.49) | 1.09 (0.82, 1.43) | 1.11 (0.84, 1.46) |
| 6 to ≤8 | 1.83 (1.19, 2.81) | 1.91 (1.24, 2.95) | 2.01 (1.54, 2.63) | 1.70 (1.29, 2.24) |
| 9 to ≤13 | 2.28 (1.49, 3.50) | 2.14 (1.39, 3.30) | 3.10 (2.32, 4.15) | 2.47 (1.84, 3.33) |
| 14 to ≤25 | 4.78 (3.12, 7.33) | 3.80 (2.46, 5.88) | 6.03 (4.22, 8.62) | 3.77 (2.60, 5.45) |
| ≥25 | 6.06 (3.70, 9.93) | 4.31 (2.60, 7.14) | 9.19 (5.90, 14.30) | 5.28 (3.32, 8.37) |

TABLE 3

Hazard Ratios for Association of logNT-proBNP with Heart Failure: The ARIC Study, 4th Examination

| NT-proBNP (pg/mol) | Men | | Women | |
|---|---|---|---|---|
| Model Factors | Age, race, cTnT | Full ARIC, cTnT | Age, race, cTnT | Full ARIC, cTnT |
| 32.9 (Q1)* | 1 | 1 | 1 | 1 |
| 66.7 (Q2)* | 1.44 (1.36, 1.52) | 1.38 (1.30, 1.46) | 1.38 (1.29, 1.48) | 1.38 (1.29, 1.48) |
| 127.7 (Q3)* | 2.01 (1.81, 2.24) | 1.86 (1.66, 2.08) | 1.86 (1.63, 2.12) | 1.86 (1.63, 2.12) |

*Three NT-proBNP values (32.9 pg/mL, 66.7 pg/mL and 127.7 pg/mL), which represent the 25th, 50th, and 75th percentiles, were chosen as examples to demonstrate the hazards for the association of logNT-proBNP and HF incidence.

The hazard ratio for incident HF increased with increasing cTnT levels, with a hazard ratio of 4.31 (95% CI 2.6, 7.14) in men and 5.28 (95% CI 3.32, 8.37) in women for cTnT values >25 ng/L (0.025 pg/L) (Table 2). Similarly, NT-proBNP levels were associated positively with incident HF in both men and women when model factors were minimally or fully adjusted (Table 3).

Example 4. Comparison of HF Risk Prediction Models with and without Integration of Biomarker Data To determine whether integration of biomarker data would improve the accuracy of HF prediction, the improvement in the ability of each model to predict HF was evaluated using statistical measures of discrimination and calibration at 10 years of follow up. Statistical measures included improvements in the area under the receiver operator characteristics curve (AUC), net reclassification index (NRI), integrated discrimination index (IDI), while accounting for censoring. In describing the NRI, given that there are no previously described HF risk categories, coronary heart disease risk prediction categories were used, namely, 0-5%, 5-10%, 10-20% and >20% of 10-year risk. Additionally, "continuous NRI" was calculated as recently described (Pencina, et al., 2011, *Stat Med.* 30(1): 11-21). Bootstraps (n=1000) were performed in order to adjust for the over optimism that can occur when the fit of the model is tested in the same data in which it is described, and to furnish the 95% confidence intervals. (Harrell, et al., 1996, *Stat Med.* 15:361-87). In terms of the statistical metrics assayed, the best model to predict HF risk was that which combined data from both biomarkers cTnT and NT-proBNP to the ARIC HF model, which includes all tested patient variables. Adding cTnT and log(NT-proBNP) data to the ARIC HF model showed a strong improvement, increasing the AUC from 0.779 to 0.836 in men and from 0.776 to 0.817 in women, with a resultant NRI of 19.6% in men and 19.9% in women. In all, about 38% of men and 31% of women were reclassified through the addition of cTnT and log NT-proBNP to the ARIC HF model. A comparison of the ARIC model vs. the ARIC+cTnT+log(NT-proBNP) model resulted in a continuous NRI of 54.7% for men and 50.7% for women (Table 4). The inclusion of additional patient variables between the age, race+cTnT+log(NT-proBNP) model and the ARIC+cTnT+log(NT-proBNP) model improved the accuracy of the HF prediction. Addition of cTnT to a model that included the ARIC HF model+NT-proBNP improved risk prediction, as did adding NT-proBNP to a model that included ARIC HF model+cTnT (Table 4, Rows 4-5). Each of these biomarkers, individually and most notably in combination, significantly improve the accuracy of the ARIC HF prediction model.

TABLE 4

Model Direct Comparisons with Differences in AUC, Net Reclassification Indices and Integrated Discrimination Indices

| Model Comparisons | AUC difference, 95% CI | IDI | NRI (%) | Continuous NRI (%) | % reclassified |
|---|---|---|---|---|---|
| | | | Men | | |
| ARIC vs. ARIC + cTnT + log(NT-proBNP) | 0.057 (0.044, 0.073) | 0.101 (0.079, 0.132) | 19.6 (12.4, 28.3) | 54.7 (42.8, 67.6) | 37.9 |
| ARIC vs. Age, race + cTnT + log(NT-proBNP) (lab model) | 0.010 (−0.015, 0.032) | 0.029 (−0.007, 0.063) | −3.7 (−14.6, 8.0) | 2.1 (−18.1, 18.9) | 56.4 |

TABLE 4-continued

Model Direct Comparisons with Differences in AUC, Net Reclassification Indices and Integrated Discrimination Indices

| Model Comparisons | AUC difference, 95% CI | IDI | NRI (%) | Continuous NRI (%) | % reclassified |
|---|---|---|---|---|---|
| Age, race + cTnT + log (NT-proBNP) (lab model) vs. ARIC + cTnT + log (NT-proBNP) | 0.047 (0.036, 0.063) | 0.073 (0.057, 0.098) | 24.5 (15.9, 32.6) | 53.9 (47.4, 70.8) | 40.4 |
| ARIC + cTnT vs. ARIC + cTnT + log (NT-proBNP) | 0.025 (0.016, 0.035) | 0.049 (0.032, 0.071) | 7.5 (2.1, 15.0) | 41.5 (29.9, 55.7) | 27.3 |
| ARIC + log (NT-proBNP) vs. ARIC + cTnT + log (NT-proBNP) | 0.014 (0.008, 0.023) | 0.031 (0.018, 0.048) | 8.29 (0.1, 11.9) | 23.1 (4.2, 41.9) | 20.0 |
| Women | | | | | |
| ARIC vs. ARIC + cTnT + log (NT-proBNP) | 0.040 (0.030, 0.055) | 0.078 (0.060, 0.104) | 19.9 (12.0, 28.3) | 50.7 (38.8, 62.3) | 31.5 |
| ARIC vs. Age, race + cTnT + log (NT-proBNP) (lab model) | −0.009 (−0.034, 0.012) | 0.023 (−0.009, 0.052) | −4.9 (−16.4, 6.3) | −8.1 (−27.6, 6.3) | 48.9 |
| age, race + cTnT + log (NT-proBNP) (lab model) vs. ARIC + cTnT + log (NT-proBNP) | 0.050 (0.038, 0.068) | 0.055 (0.042, 0.080) | 27.5 (19.2, 36.2) | 66.1 (55.3, 78.0) | 36.7 |
| ARIC + cTnT vs. ARIC + cTnT + log (NT-proBNP) | 0.012 (0.006, 0.022) | 0.027 (0.015, 0.042) | 7.3 (1.5, 14.0) | 24.5 (15.8, 39.4) | 20.9 |
| ARIC + log (NT-proBNP) vs. ARIC + cTnT + log (NT-proBNP) | 0.012 (0.005, 0.022) | 0.030 (0.016, 0.047) | 7.3 (0.1, 13.6) | 39.7 (16.3, 60.0) | 21.6 |

Example 5. Comparison of Simplified Lab Models to Clinical HF Models

The various models were described by decile of estimated risk and the estimated percentage of HF events occurring within each decile. The lab model, which accounted for age, race, and both cTnT and NT-proBNP, was comparable to the ARIC HF model without biomarkers, with no statistically significant differences in AUC, NRI or IDI (Table 5). This result shows that the simplified lab model with a subset of patient variables can predict HF with comparable accuracy to the clinical ARIC model.

The ARIC model, lab model, and ARIC+cTnT+log(NT-proBNP) model shared estimated risk values in both men (FIGS. 1A and 1B) and women (FIGS. 2A and 2B), wherein about 60-75% of the incident HF events occurred in the highest three deciles of estimated risk (greater than about 10% 10-year risk in men and greater than about 7% 10-year risk in women).

The models were further tested using the Gronnesby-Borgan test statistic, which evaluates model fits. Gronnesby & Borgan, 1996, *Lifetime Data Anal.*, 2:315-28. Significant 'p' values are associated with poor model fits. The results are shown in Table 5. The model fit scores for ARIC model, lab model, and ARIC+cTnT+log(NT-proBNP) model are all comparable in men (Table 5, col. 3), supporting the ability of the simpler lab model to predict HF risk with comparable accuracy to the clinical ARIC HF model.

TABLE 5

Area Under the Receiver Operator Characteristics Curve and the Evaluation of Fit Test Statistic

| Model Factors | Area Under the Receiver Operator Characteristics Curve (AUC) | | Evaluation of Model Fit: Grønnesby-Borgan Test Statistic | |
|---|---|---|---|---|
| | Men | Women | Men | Women |
| Model 1: Age, race only (no biomarkers) | 0.653 (0.628, 0.676) | 0.658 (0.634, 0.682) | 9.33 (p = 0.41) | 18.32 (p = 0.03) |

TABLE 5-continued

Area Under the Receiver Operator Characteristics Curve and the Evaluation of Fit Test Statistic

| Model Factors | Area Under the Receiver Operator Characteristics Curve (AUC) | | Evaluation of Model Fit: Grønnesby-Borgan Test Statistic | |
|---|---|---|---|---|
| | Men | Women | Men | Women |
| Model 2: ARIC model (no biomarkers) | 0.779 (0.763, 0.800) | 0.776 (0.760, 0.797) | 18.12 (p = 0.03) | 21.91 (p = 0.01) |
| Model 3: Age, Race, + cTnT + NT-proBNP (lab model) | 0.789 (0.767, 0.812) | 0.767 (0.745, 0.789) | 14.35 (p = 0.11) | 5.80 (p = 0.76) |
| Model 4: ARIC model + cTnT + NT-proBNP | 0.836 (0.821, 0.857) | 0.817 (0.803, 0.837) | 14.60 (p = 0.10) | 18.31 (p = 0.03) |
| ARIC model (Model 2) + cTnT | 0.811 (0.797, 0.833) | 0.804 (0.790, 0.825) | 15.95 (p = 0.07) | 20.39 (p = 0.02) |
| ARIC model (Model 2) + NT-proBNP | 0.822 (0.805, 0.843) | 0.804 (0.789, 0.826) | 7.96 (p = 0.54) | 19.64 (p = 0.02) |

Example 6. Identification of Potential cTnT and NT-proBNP Cut-Points

Potential cTnT and NT-proBNP cut-points were identified by defining both an unweighted and weighted Youden's index (Youden et al., 1950, *Cancer*, 3: 32-35). The unweighted Youden's index was defined as (sensitivity+specificity)−1 while the weighted Youden's index was described by giving higher importance to either sensitivity 2*(0.75*sensitivity+0.25*specificity)−1 or specificity 2*(0.25*sensitivity+0.75*specificity)−1 to evaluate potential cut points to "rule out" and "rule in" incident HF occurrence. Participants with levels below the detectable limit were assigned half the lower limit of detection for calculation of the mean. Because of the continuous, rather monotonic association of cTnT and NT-proBNP with HF events (FIGS. 3.1 and 3.2), no obvious cut-points emerged for immediate identification.

However, to enable identification of potential cTnT and NT-proBNP cut-points, individuals were classified by number of risk factors and whether or not they developed HF. We classified individuals as "stage A" HF risk if the individual showed the presence of any of the following: hypertension, diabetes, obesity, metabolic syndrome and prevalent cardiovascular disease) and individuals with no risk factors were referred to as stage 0 for simplicity. We then described the cTnT and NT-proBNP distribution by HF stage and incident HF status. (Tables 6 and 7). When cTnT was considered almost all individuals who developed HF had a detectable concentration of cTnT (Table 6). This result strongly suggested that an undetectable cTnT level has a high negative predictive value. With three risk factors, men and women who did not develop incident HF had mean cTnT values of ~11 ng/L and ~6 ng/L, respectively. This was similar to the mean values for those with no risk factors who developed HF (~10 ng/L in men and ~6 ng/L in women)(Table 6). In those who developed incident HF, the values were higher with increasing risk factors, suggesting that these cut-points (10 ng/L in men and 6 ng/L in women) represent potential cut-points for cTnT values in the prediction of HF.

Similar results were observed when NT-proBNP was considered (Table 7). For NT-proBNP levels, the geometric mean was calculated as exp (average (log (NT-proBNP)).

TABLE 6

Cardiac troponin T (cTnT) by presence/absence of stage A heart failure (HF) and incident HF status: the ARIC study

| | | Men | | | | Women | | | | Overall | | | |
|---|---|---|---|---|---|---|---|---|---|---|---|---|---|
| | | N | | Mean cTnT, ng/L | | N | | Mean cTnT, ng/L | | N | | Mean cTnT, ng/L | |
| HF status | HF stage | Overall | Detectable cTnT | Overall* | Detectable cTnT | Overall | Detectable cTnT | Overall* | Detectable cTnT | Overall | Detectable cTnT | Overall* | Detectable cTnT |
| Did not develop HF | 0† | 1122 | 839 | 6 | 8 | 1383 | 626 | 3 | 6 | 2505 | 1465 | 5 | 7 |
| | A | 2755 | 2347 | 9 | 10 | 3638 | 2040 | 4 | 7 | 6393 | 4387 | 6 | 8 |
| Developed HF | 0† | 43 | 41 | 10 | 10 | 42 | 30 | 6 | 8 | 85 | 71 | 8 | 9 |
| | A | 449 | 424 | 18 | 19 | 436 | 330 | 10 | 13 | 885 | 754 | 14 | 16 |

TABLE 7

N-terminal pro-B-type natriuretic peptide (NT-proBNP) values by presence/absence of stage A HF and incident HF status: the ARIC study

| | | Men | | Women | | Overall | |
|---|---|---|---|---|---|---|---|
| HF status | HF stage | Geometric mean NT-proBNP overall,* pg/mL | Geometric mean of detectable NT-proBNP, pg/mL | Geometric mean NT-proBNP overall,* pg/mL | Geometric mean of detectable NT-proBNP, pg/mL | Geometric mean NT-proBNP overall,* pg/mL | Geometric mean of detectable NT-proBNP, pg/mL |
| Did not develop HF | 0† | 36.41 | 42.36 | 79.08 | 80.89 | 55.87 | 61.01 |
| | A | 46.79 | 55.85 | 70.20 | 74.73 | 58.94 | 66.11 |
| Developed HF | 0† | 88.01 | 88.01 | 126.73 | 126.73 | 105.38 | 105.38 |
| | A | 120.35 | 131.46 | 128.41 | 130.76 | 124.26 | 131.11 |

What is claimed is:

1. A method for diagnosing heart failure risk in a subject, the method consisting essentially of:
   (a) obtaining the subject's simplified model factors, wherein the simplified model factors are (i) age and race; or (ii) age, race and gender;
   (b) obtaining the amount of Troponin T (TnT) and the amount of NT-pro B-type natriuretic peptide (NT-proBNP) in a serum or plasma sample obtained from the subject;
   (c) calculating a simplified model score, using a computer comprising an evaluation unit, based on the amount of TnT and the amount of NT-proBNP in the biological sample obtained from the subject and the subject's simplified model factors, wherein the evaluation unit comprises a database with stored reference amounts of TnT and NT-proBNP and a computer program code; and
   (d) providing a diagnosis of heart failure risk based on the simplified model score calculated in step c).

2. The method of claim 1, wherein step (b) is performed by the following steps:
   i) contacting a portion of the serum or plasma sample obtained from the subject with an antibody Immunoreactive for Troponin T (TnT);
   ii) contacting a portion of the serum or plasma sample obtained from the subject with an antibody Immunoreactive for a NT-pro B-type natriuretic peptide (NT-proBNP); and
   iii) determining an amount of TnT and an amount of NT-proBNP in the serum or plasma sample obtained from the subject.

3. The method of claim 2, further comprising using an evaluation unit to compare the determined amount of TnT with a suitable reference TnT amount for predicting a risk of heart failure.

4. The method of claim 2, further comprising using an evaluation unit to compare the determined amount of NT-proBNP with a suitable reference NT-proBNP amount for predicting a risk of heart failure.

5. The method of claim 3 or 3, wherein the evaluation unit is an evaluation computer comprising:
   a database with stored reference amounts containing suitable reference amounts of TnT and NT-proBNP; and
   computer program code which, when tangibly embedded on the evaluation computer, carries out the comparison of the determined amount of TnT or NT-proBNP and the corresponding stored reference amounts.

6. The method of claim 2, wherein the evaluation unit further comprises control strips or tables allocating the determined amount of TnT and/or NT-proBNP to a reference amount.

7. The method of claim 1, wherein the subject is human.

8. The method of claim 1, wherein the simplified model factors obtained in step (a) are age and race.

9. The method of claim 1, wherein the simplified model factors obtained in step (a) are age, race and gender.

10. The method of claim 1, the amount of Troponin T (TnT) and/or the amount of NT-pro B-type natriuretic peptide (NT-proBNP) in the serum or plasma sample is obtained using an analyzing unit.

11. The method of claim 10, wherein the analyzing unit comprises at least one of aptamers and antibodies.

* * * * *